US012313539B2

(12) United States Patent
Al-Naib

(10) Patent No.: US 12,313,539 B2
(45) Date of Patent: May 27, 2025

(54) TERAHERTZ ASYMMETRIC S-SHAPED COMPLEMENTARY METASURFACE BIOSENSOR FOR GLUCOSE CONCENTRATION

(71) Applicant: Imam Abdulrahman Bin Faisal University, Dammam (SA)

(72) Inventor: Ibraheem Al-Naib, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 266 days.

(21) Appl. No.: 18/311,609

(22) Filed: May 3, 2023

(65) Prior Publication Data

US 2024/0369477 A1    Nov. 7, 2024

(51) Int. Cl.
| | | |
|---|---|---|
| *G01N 21/35* | (2014.01) | |
| *G01N 21/3577* | (2014.01) | |
| *G01N 21/3581* | (2014.01) | |
| *G01N 33/49* | (2006.01) | |

(52) U.S. Cl.
CPC ..... *G01N 21/3581* (2013.01); *G01N 21/3577* (2013.01); *G01N 33/49* (2013.01)

(58) Field of Classification Search
CPC . G01N 21/3581; G01N 21/3577; G01N 33/49
See application file for complete search history.

(56) References Cited

U.S. PATENT DOCUMENTS

| | | | |
|---|---|---|---|
| 8,271,241 B2 | 9/2012 | Akyurtlu et al. | |
| 9,683,991 B2 | 6/2017 | Xiong et al. | |
| 10,288,563 B1 | 5/2019 | Ahmadivand | |
| 11,041,802 B2 | 6/2021 | Al-Naib | |
| 2013/0207737 A1* | 8/2013 | Weldon | H01Q 15/0086 333/23 |

FOREIGN PATENT DOCUMENTS

CN    113418855 A    9/2021

OTHER PUBLICATIONS

Saleh et al. (Glucose Level Sensing Using Single Asymmetric Split Ring Resonator, MDPI, Sensors 2021, 21, 2945, https://doi.org/10.3390/s21092945, Received: Mar. 7, 2021, Accepted: Apr. 19, 2021 Published: Apr. 22, 2021) (Year: 2021).*

(Continued)

*Primary Examiner* — Hugh Maupin
(74) *Attorney, Agent, or Firm* — Oblon, McClelland, Maier & Neustadt, L.L.P.

(57) ABSTRACT

An asymmetric S-shaped complementary metasurface biosensor for sensing glucose concentration includes a metallic sheet for receiving a glucose sample, a first arm, and a second arm. The first arm is configured as an S-shaped slot. The second arm is configured to be an S-shaped slot which is a smaller mirror image of the first arm. Electromagnetic coupling between the asymmetric S-shaped slots leads to the excitation of the resonances. An asymmetric resonance is excited that features a very small bandwidth when a terahertz radiation is swept across the metallic sheet. A redshift in the response is indicative of a glucose concentration in the glucose sample.

20 Claims, 15 Drawing Sheets

(56) References Cited

OTHER PUBLICATIONS

Babu et al. ; A Triple-Band Reflective Polarization Conversion Metasurface with High Polarization Conversion Ratio for lsm and X-Band Applications ; MDPI sensors, 22 ; Oct. 26, 2022 ; 12 Pages.
Jung et al. ; Anisotropy Modeling of Terahertz Metamaterials: Polarization Dependent Resonance Manipulation by Meta-Atom Cluster ; Scientific Reports 4 ; Jun. 9, 2014 ; 7 Pages.
Al-Naib et al. ; Terahertz Asymmetric S-Shaped Complementary Metasurface Biosensor for Glucose Concentration ; MDPI biosensors, 12 ; Aug. 6, 2022 ; 11 Pages.
Born et al. ; Laser beam machined free-standing terahertz metamaterials ; The Institution of Engineering and Technology ; Feb. 23, 2015 ; 2 Pages.

* cited by examiner

TERAHERTZ ASYMMETRIC S-SHAPED COMPLEMENTARY METASURFACE BIOSENSOR FOR GLUCOSE CONCENTRATION

STATEMENT REGARDING PRIOR DISCLOSURE BY THE INVENTORS

Aspects of this technology are described in an article "Terahertz Asymmetric S-Shaped Complementary Metasurface Biosensor for Glucose Concentration" published in Biosensors 2022, Vol. 12, pp 609, on Aug. 6, 2022, which is incorporated herein by reference in its entirety.

STATEMENT OF ACKNOWLEDGEMENT

The inventor acknowledges the financial support provided by the Imam Abdulrahman bin Faisal University Deputyship for Research & Innovation, Ministry of Education in Saudi Arabia, through the project number IF-2020-013-Eng.

BACKGROUND

Technical Field

The present disclosure is directed to a terahertz asymmetric S-shaped complementary metasurface biosensor for measuring glucose concentration.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Diabetes is a major chronic disease that threatens the health and lives of people. In 2019, the World Health Organization and the international diabetes federation reported that diabetes cases reached 463 million worldwide, resulting in a demand for convenient monitoring of glucose levels in the blood. When fasting, the normal glucose range should be between 70 and 120 mg/dL. However, with glucose levels that are lesser or greater than the normal glucose range, the patient is identified as having hypoglycemia and hyperglycemia, respectively. Failing to maintain glucose levels in the aforementioned range may result in many health problems including cardiovascular diseases, renal failure, and peripheral neuropathy. Self-monitoring of blood glucose (SMBG) is essential for a diabetic person or health care professionals to take appropriate measures to maintain a glucose level within the aforementioned glucose range.

A conventional SMBG method requires a small blood sample from the patient, e.g., from a finger prick. The blood sample is placed on a test strip and inserted into a glucose meter that analyzes the blood sample on the test strip and provides a blood glucose level. Unfortunately, to monitor the blood glucose levels, the patient may need to prick his fingers multiple times within a day, which may be painful and inconvenient. Additionally, measurements with the conventional SMBG method are prone to errors due to various factors including sample quality, human error, calibration, humidity, and hygiene in a sample area.

Any change in glucose concentration in blood has an impact on the dielectric properties of blood, therefore the blood glucose concentration exhibits a response characteristic to electromagnetic signals. Therefore, electromagnetic waves can be used as a blood glucose detection technique. For testing an electromagnetic constant of blood, an existing method uses a coaxial probe as a sensor, however this method is not sensitive to slight changes of blood glucose concentration, decreasing the detection accuracy.

Terahertz rays (THz or T-rays) are a unique type of electromagnetic radiation. THz technology has about 4.14 meV photon energy at 1 THz, and it is completely safe for users. Several unique features make THz-based technology suitable for medical applications. The characteristic energies of rotational and vibrational motions of molecules can be observed in the THz frequency region. As a result, many chemical and biological molecules can be identified by their characteristic resonant peaks in the THz frequency region. The electromagnetic field has to be confined in order to increase the THz wave-sample interaction. To provide a required interaction, a metasurface structure has been employed. The metasurface has highly sensitive response characteristics and strong control ability to the phase and amplitude of electromagnetic waves and can accurately reflect the reflection or transmission characteristics of blood sugar to electromagnetic waves.

A redshift of the resonance frequency occurs as a result of dielectric environment modification when the metasurface is coated with a blood sample. This redshift is utilized as a metric for its refractive index and can be used to identify the analyte type or its concentration. An existing TDS spectrometer has been described that investigates non-invasive glucose level sensing in reflective mode using reflection of THz pulse from nail plate/nail bed interface. (See: Gusev, S. I.; Demchenko, P. S.; Cherkasova, O. P.; Fedorov, V. I., Khodzitsky, M. K, "*Influence of glucose concentration on blood optical properties in THz frequency range*", Chin. Opt. 2018, 11, 182-189, incorporated herein by reference in its entirety). The TDS spectrometer reveals that the peak-to-peak amplitude of the pulse reflected from the nail plate/nail bed changes with varying glucose levels. However, the thickness of a nail plate varies from person to person, thereby limiting the accuracy of the TDS spectrometer. A conventional resonator for sensing glucose concentration using a symmetric complementary split rectangular resonator under oblique THz wave excitation has been used. The resonator achieves a resonance frequency shift of resonance frequency at 0.506 THz was 122 GHz for a glucose concentration of 342 mg/dL for a 5 μm thick sample. (See: Ibraheem Al-Naib, "*Sensing glucose concentration using symmetric metasurfaces under oblique incident terahertz waves*", Crystals 2021, 11, incorporated herein by reference in its entirety). The resonator with an overlayer thickness of 20 μm revealed a wavelength sensitivity of 140,000 nm/RIU. The resonance frequency shift is used as a measure of the changes in the glucose level of the samples. However, the conventional resonator has a limitation to provide a sensitivity of 75,700 nm/RIU only.

U.S. Pat. No. 11,041,802B2 describes an E-shaped metamaterial biosensor which responds under a range of terahertz frequencies. A terahertz receiver is connected to a controller which matches the frequency response to identify a biomolecule type. The working principle of the E shaped metamaterial biosensor is amplitude difference referencing technique (ADRT). In the amplitude difference referencing technique, the frequency response of an uncoated metasurface is subtracted from the frequency response of a coated metasurface without normalization. Further, the E-shaped metamaterial biosensor additionally requires a substrate, resulting in a complex structure that needs a particular construction technique.

Hence, there is a need for a terahertz metasurface which has a high-quality factor and high sensitivity for biosensing.

SUMMARY

In an exemplary embodiment, an asymmetric S-shaped complementary metasurface biosensor for sensing glucose concentration is described. The biosensor includes a metallic sheet, a first arm, and a second arm. The metallic sheet is configured to receive a glucose sample. The first arm is configured as an S-shaped slot in the metallic sheet. The first arm is configured to have a length $l_1$ and a width equal to one half of the length $l_1$. The second arm is spaced apart from the first arm by a gap g. The second arm is configured to be an S-shaped slot in the metallic sheet which is a mirror image of the first arm. The second arm is configured to have a length $l_2$. The length $l_2=l_1-d$, where d ranges from about 1% of $l_1$ to about 15% of $l_1$, and to have a width equal to one half of the length $l_2$. The first arm and the second arm are configured to resonate at an asymmetric resonant frequency when a terahertz radiation is swept in a direction normal to the metallic sheet. A redshift in the asymmetric resonant frequency is indicative of a glucose concentration in the glucose sample.

In another exemplary embodiment, a system for measuring glucose concentration of an analyte is described. The system includes an asymmetric S-shaped complementary metasurface biosensor, a terahertz radiation source, a terahertz receiver, a database, and a controller. The asymmetric S-shaped complementary metasurface biosensor includes a metallic sheet, a first arm, and a second arm. The metallic sheet is configured to receive a glucose sample. The first arm is configured as an S-shaped slot in the metallic sheet. The first arm has a length $l_1$ and a width equal to one half of the length $l_1$. The second arm is spaced apart from the first arm by a gap g. The second arm is configured to be an S-shaped slot in the metallic sheet which is a mirror image of the first arm. The second arm has a length $l_2$, wherein the length $l_2=l_1-d$, where d ranges from about 1% of $l_1$ to about 15% of $l_1$, and to have a width equal to one half of the length $l_2$. The terahertz radiation source has a range of frequencies. The terahertz radiation source is configured to sweep a terahertz radiation beam at the range of frequencies in a normal direction to the metallic sheet such that an electromagnetic coupling between the first arm and the second arm excites an asymmetric resonance frequency. The terahertz receiver is configured to receive light beams transmitted through the asymmetric S-shaped complementary metasurface biosensor and generate electrical signals indicative of a redshift in the asymmetric resonance frequency.

A database includes records relating the redshift to glucose concentration in the analyte. The controller is operatively connected to the terahertz radiation source. The terahertz radiation receiver, and the database. The controller has circuitry, a memory storing program instructions and at least one processor configured to execute the program instructions to: activate the terahertz radiation source to project the terahertz radiation beam at the range of frequencies onto the metallic sheet; receive the electrical signals from the receiver; and match the redshift to a record in the database which identifies the glucose concentration of the analyte.

In another exemplary embodiment, a sensor system for determining a concentration of an analyte in a test sample is described. The sensor system includes an asymmetric S-shaped complementary metasurface sensor, a terahertz radiation source, a terahertz receiver, a database, and a controller. The asymmetric S-shaped complementary metasurface sensor includes a metallic sheet, a transparent casing, an opening, a first arm, and a second arm. The metallic sheet includes a first edge, a second edge parallel to the first edge, a third edge perpendicular to the first edge and the second edge, a fourth edge parallel to the third edge, a first central axis extending from the first edge to the second edge, and a second central axis extending from the third edge to the fourth edge. The transparent casing is configured to hold the metallic sheet. The opening is located in the transparent casing to receive the test sample. The transparent casing is configured such that the glucose sample coats at least one of the front surface and the back surface of the metallic sheet. The first arm is configured as an S-shaped slot in the metallic sheet, wherein the first arm has a length $l_1$ and a width equal to one half of the length $l_1$. The second arm is spaced apart from the first arm by a gap g. The second arm is configured as an S-shaped slot in the metallic sheet which is a mirror image of the first arm. The second arm has a length $l_2$, wherein the length $l_2=l_1-d$, where d ranges from about 1% of $l_1$ to about 15% of $l_1$, and to have a width equal to one half of the length $l_2$. A terahertz radiation source has a range of frequencies. The terahertz radiation source is configured to sweep a terahertz radiation beam at the range of frequencies normal to the metallic sheet such that an electromagnetic coupling between the first arm and the second arm excites an asymmetric resonance frequency.

A terahertz receiver is configured to receive light beams transmitted through the asymmetric S-shaped complementary metasurface biosensor and generate electrical signals indicative of a redshift in the asymmetric resonance frequency.

A database includes records relating the redshift to the concentration of the analyte in the test sample. The controller operatively connected to the terahertz radiation source, the terahertz radiation receiver, and the database, wherein the controller has circuitry, a memory storing program instructions and at least one processor configured to execute the program instructions to: activate the terahertz radiation source to project the terahertz radiation beam at the range of frequencies onto the metallic sheet; receive the electrical signals from the receiver; and match the redshift to a record in the database which identifies the analyte concentration.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
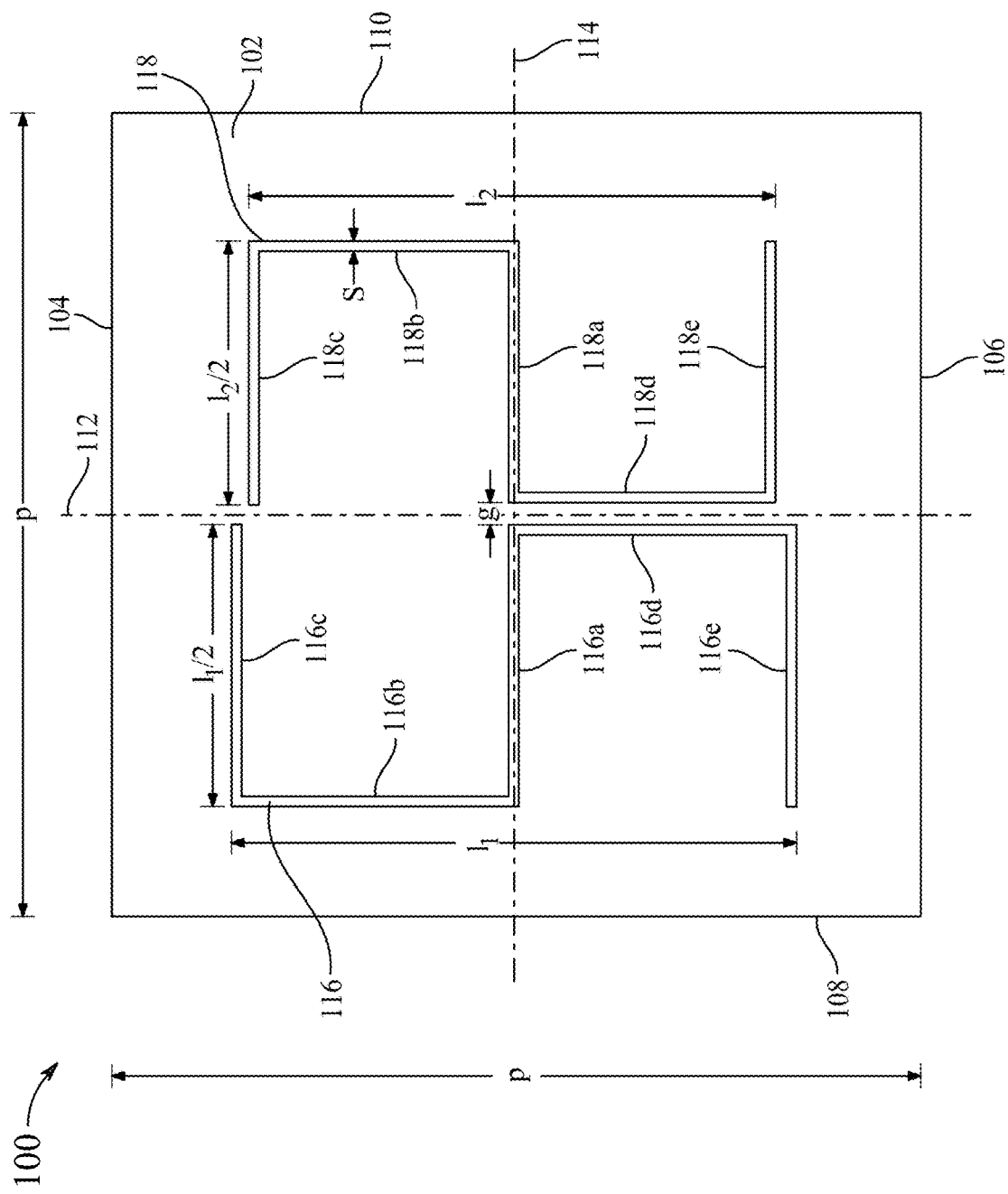
FIG. 1A is a front view of an asymmetric S-shaped complementary metasurface biosensor, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

A redshift is defined as an increase in the wavelength, and corresponding decrease in the frequency and photon energy, of electromagnetic radiation, such as light. The opposite change, a decrease in wavelength and simultaneous increase in frequency and energy, is known as a negative redshift, or blueshift. The terms derive from the colors red and blue which form the extremes of the visible light spectrum.

In aspects of the present disclosure, a measurement of the redshift is used to identify a concentration of glucose in a blood sample.

Aspects of this disclosure are directed to a terahertz metasurface glucose concentration level biosensor. The biosensor includes an asymmetric S-shaped complementary resonator. In a design configuration, the biosensor is a free-standing metasurface, and hence a layer of sample can be applied as an analyte on a front surface of the metasurface, or the metasurface can be immersed inside the sample such that the biosensor has a layer on the front surface and another layer on the back surface. A resulting redshift in a resonance frequency of 110.6 GHz occurs when the front surface of the sample is as small as 2 μm with a glucose concentration level as low as 54 mg/dL, which is a significant shift that can be easily identified. Moreover, increasing the glucose concentration level to 342 mg/dL and using a 20 μm thick layer on the top surface of the biosensor and on the bottom surface of the biosensor, increased the redshift to 286.6 GHZ, which is almost three times compared with the 2 μm sample and concentration of 54 mg/dL. The biosensor of the present disclosure is wavelength sensitive (more than 322,000 nm/RIU (Refractive index unit)).

Figure 1B:
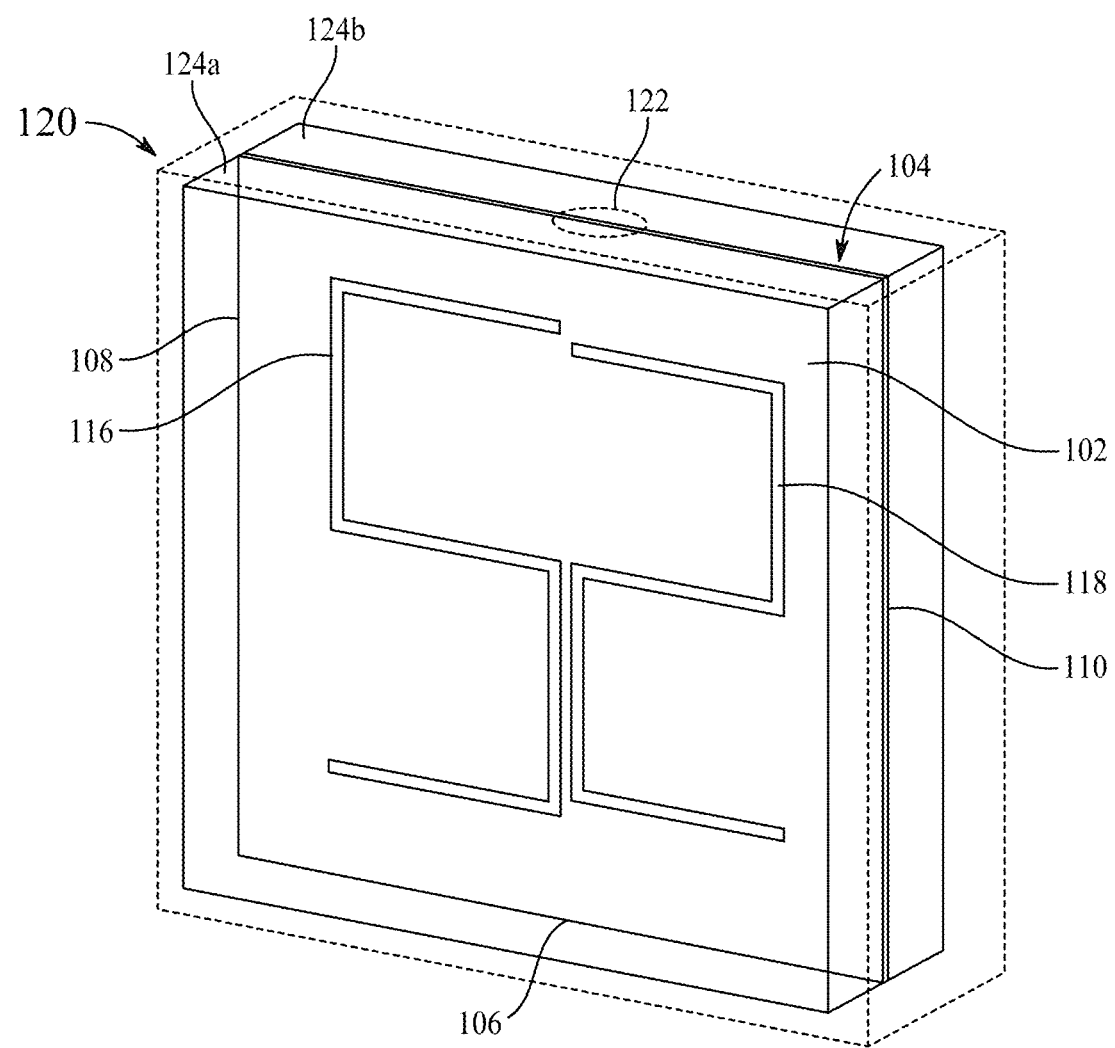
FIG. 1B is a three-dimensional representation of the biosensor placed in a transparent casing, according to certain embodiments.

FIG. 1A-FIG. 1B illustrate the overall configuration of an asymmetric S-shaped complementary metasurface biosensor for sensing glucose concentration.

FIG. 1A is a front view of the asymmetric S-shaped complementary metasurface biosensor 100 (hereinafter interchangeably referred to as "the biosensor 100" and also known as "the metasurface 100"), according to one or more aspects of the present disclosure. FIG. 1A shows a two-dimensional (2 D) configuration (also known as a unit cell) of the biosensor 100. Each unit cell includes an S-shaped complementary resonator (SCR) with two arms, where one arm is a smaller mirrored version of the other arm. In the drawings of FIG. 1A-FIG. 1B, the dimensions of the unit cell shown are for the example a biosensor having dimensions (p is referred to as the periodicity of the unit cell) of p μm×p μm (microns) should not be construed as limiting. For a metasurface of less than p μm×p μm, the dimensions are proportionately smaller and for a metasurface of greater than p μm×p μm, the dimensions are proportionately bigger.

In operation, a terahertz radiation beam is swept across the biosensor. The terahertz waves are applied normal to the metasurface. Electromagnetic coupling between the S-shaped slots leads to the excitation of a response which includes resonance of each of the arms at specific resonances. When both S-shaped slots are symmetric, that is, $l_1$ is equal to $l_2$, a dipole symmetric resonance mode is excited. When the symmetry is broken by reducing $l_2$, an asymmetric resonance mode is excited that features a very small bandwidth when a terahertz radiation is swept in a normal direction to the metallic sheet.

The dipole symmetric mode is shifted a little bit towards high frequencies. For a given glucose sample, the concentration is fixed. Hence, there is no direct relation between the resonance frequency and the concentration of the glucose sample. However, the redshift in the resonance frequency is used as a measure for the concentration of the glucose sample.

As shown in FIG. 1A, the biosensor 100 includes a metallic sheet 102, a first arm 116, and a second arm 118. The metallic sheet 102 is formed of a highly reflective material.

The metallic sheet 102 is configured to receive a glucose sample from a user. In an example, the user can store the glucose sample in a container, such as a pen which "sticks" the user to draw blood. Alternatively, the user can dip the biosensor 100 into the glucose sample, apply the glucose sample to the biosensor in the form of droplets, or the glucose sample can be drawn into a casing of the metasurface by capillary action. In an aspect, the metallic sheet 102 includes two surfaces i.e., a front surface, and a back surface. The metallic sheet 102 is configured to receive the glucose sample at the front surface of the metallic sheet 102 or to be immersed in the glucose sample. In an example, the metallic sheet 102 is configured to be immersed in the container having the glucose sample such that the front surface and the back surface of the metallic sheet 102 contact the glucose sample. The container is transparent to terahertz radiation. In an aspect, the container is a cuvette which is transparent to terahertz radiation. In an aspect, the metallic sheet 102 is one of an aluminum sheet, a copper sheet, a gold sheet, a graphene sheet and a silver sheet. For example, the metallic sheet 102 is preferably an aluminum sheet. In an aspect, the metallic sheet 102 has a thickness of 200 nanometers (nm). In some example, the metallic sheet 102 may have different dielectric constant values such that the biosensor is configured to cover different frequencies of a wide range of glucose level concentrations.

As shown in FIG. 1A, the metallic sheet 102 includes a first edge 104, a second edge 106, a third edge 108, and a fourth edge 110. In an example, the metallic sheet 102 has a thickness of about 200 nanometers and is configured in a square shape having a periodicity of about 200 microns. The second edge 106 is parallel to the first edge 104. The third edge 108 is perpendicular to the first edge 104 and the second edge 106. The fourth edge 110 is parallel to the third edge 108. A first central axis 112 extends from the first edge 104 to the second edge 106. A second central axis 114 extends from the third edge 108 to the fourth edge 110.

The first arm 116 is configured as an S-shaped slot in the metallic sheet 102. In an aspect, a width of the S-shaped slot is about 3 microns. The first arm 116 has a length $l_1$ and a width equal to one half of the length $l_1$. In an aspect, the length $l_1$ is about 140 microns. As shown in FIG. 1A, the first arm 116 includes a plurality of connected legs. For example, the plurality of connected legs include a first leg 116a, a second leg 116b, a third leg 116c, a fourth leg 116d, and a fifth leg 116e. The first leg 116a is coincident with the second central axis 114. A first end of the first leg 116a begins at a distance of ½ g from the first central axis 112 and the first leg 116a extends towards the third edge 108 for a distance of $l_1/2$. The second leg 116b has a first end connected to a second end of the first leg 116a. The second leg 116b is perpendicular to the first leg 116a. The second leg 116b extends towards the first edge 104 for a distance of $l_1/2$. The third leg 116c is parallel to the first leg 116a. The third leg 116c has a first end connected to a second end of the second leg 116b. The third leg 116c is perpendicular to the second leg 116b. The third leg 116c extends towards the first central axis 112 for a distance of $l_1/2$. A first end of the fourth leg 116d is connected to a second end of the first leg 116a. The fourth leg 116d is perpendicular to the first leg 116a. The fourth leg 116d extends towards the second edge 106 for a distance of $l_1/2$. The fifth leg 116e is parallel to the first leg 116a. The fifth leg 116e has a first end connected to a second end of the fourth leg 116d. The fifth leg 116e is perpendicular to the fourth leg 116d. The fifth leg 116e extends towards the third edge 108 for a distance of $l_1/2$.

The second arm 118 is configured to be the S-shaped slot in the metallic sheet 102 which is a smaller mirror image of the first arm 116. The second arm 118 is configured to have a length $l_2$. The length $l_2$ is equal to $l_1-d$, where d ranges from about 1% of $l_1$ to about 15% of $l_1$, and the second arm has a width equal to one half of the length $l_2$. In an aspect, the length $l_2$ is selected from a range of about 120 microns to about 139 microns.

The second arm 118 is spaced apart from the first arm 116 by a gap g. In an aspect, the gap is about 4.5 microns. As shown in FIG. 1A, the second arm 118 includes a plurality of connected legs. For example, the plurality of connected legs include a first leg 118a, a second leg 118b, a third leg 118c, a fourth leg 118d, and a fifth leg 118e. The first leg 118a is coincident with the second central axis 114. A first end of the first leg 118a is configured to begin at a distance of ½ g from the first central axis 112 and the first leg 118a extends towards the fourth edge 110 for a distance of $l_2/2$. The second leg 118b has a first end which is connected to a second end of the first leg 118a. The second leg 118b is perpendicular to the first leg 118a. The second leg 118b is configured to extend towards the first edge 104 for a distance of $l_2/2$. The third leg 118c is parallel to the first leg 118a. The third leg 118c has a first end connected to a second end of the second leg 118b. The third leg 118c is perpendicular to the second leg 118b. The third leg 118c is configured to extend towards the first central axis 112 for a distance of $l_2/2$. The fourth leg 118d has a first end connected to the first end of the first leg 118a. The fourth leg 118d is perpendicular to the first leg 118a. The fourth leg 118d is configured to extend towards the second edge 106 for a distance of $l_2/2$. The fifth leg 118e is parallel to the first leg 118a. The fifth leg 118e has a first end connected to a second end of the fourth leg 118d. The fifth leg 118e is perpendicular to the fourth leg 118d. The fifth leg 118e is configured to extends towards the fourth edge 110 for a distance of $l_2/2$.

In an overall aspect, an electromagnetic coupling established between the S-shaped slots (the first arm 116 and the second arm 118) leads to an excitation of a resonant frequency. An electromagnetic radiation in a frequency range from 0.1 THz to 10 THz is swept across the metallic sheet 102. If the first arm and the second arm were the same size, a dipole resonant frequency with wide bandwidth would be excited. However, as the second arm is smaller than the first arm, a redshift in the resonant frequency occurs which is an indicative of a glucose concentration in the glucose sample.

FIG. 1B is a three-dimensional (3D) representation of the biosensor 100 placed in a casing 120, according to certain embodiments. As shown in FIG. 1B, in a structural aspect, the biosensor 100 includes a casing 120 (also referred to as a container, and which may be a cuvette), and an opening 122 located in the top of the casing 120. In an aspect, the casing 120 is a transparent casing. In an aspect, the casing may have a window over the S-shaped arms which is open to the sample. The casing 120 is configured to hold the metallic sheet 102. The opening 122 is located in the casing 120 to receive the glucose sample. The casing 120 is constructed such that the glucose sample coats at least one of the front surface and the back surface of the metallic sheet 102. The casing may be constructed of any of paper, plastic, metal and the like.

FIG. 1B depicts the glucose sample deposited on the top surface (shown by 124a) and the glucose sample deposited on the back surface (shown by 124b) of the metallic sheet 102. The metallic sheet 102 can be coated with the glucose sample or immersed in the middle of the glucose sample.

Examples and Experiments

The following examples are provided to illustrate further and to facilitate the understanding of the present disclosure.

To evaluate the performance of the biosensor 100, various experiments were conducted and corresponding results (responses) were analyzed. The responses include a transmission frequency response. In an example, simulation of the biosensor 100 was performed using a simulation package Computer Simulation Technology Microwave Studio (CST MWS). CST MWS Studio Suite is a computational electromagnetics tool developed by Dassault Systèmes Simulia, located at 492 Old Connecticut Path, Suite 500, Framingham, MA 01701, USA. The CST MWS solves Maxwell equations in a frequency domain based on a finite integration technique. Excitation of a plane wave was considered with periodic boundary conditions to mimic the actual scenario.

As shown in FIG. 1A, the biosensor 100 exhibits a field polarization where an electric component is horizontally oriented, and a magnetic component is vertically oriented. When the metasurface 100 is excited by the THz waves under normal incidence, an excitation of a symmetric dipole resonance mode occurs in the metasurface 100 when the first and second arm are equal in size. When the first and second arm are asymmetric in size, the dipole resonance mode becomes asymmetric, and a redshift in the response can be measured which is indicative of a glucose concentration of the glucose sample.

The biosensor 100 is based on the utilization of a quasi-bound state in the continuum (QBIC) with a broken in-plane symmetry. In an example, the QBIC is a Fano resonant state with long optical lifetime controlled by symmetry-breaking perturbations. The biosensor 100 may be easily fabricated using a simple optical setup with a laser beam. In an example, the first arm 116 and the second arm 118 are formed using a laser beam machining technique (see: N. Born, R. Gente, I. Al-Naib, M. Koch, "*Laser beam machined free-standing terahertz metamaterials*", Electronics Letters Volume 51, Issue 13 Jun. 2015, Pages 958-1037, incorporated herein by reference in its entirety). In the laser beam machining technique, a frequency-doubled Nd:YAG laser is employed. The frequency-doubled Nd:YAG laser generates nanosecond pulses with a wavelength of 532 nm and a repetition rate of 20 Hz. Output power in a first stage is decreased from ~75 mJoule/pulse to ~4.2 mJoule/pulse. Afterwards, neutral density filters are used to reduce the power even more-depending on the required linewidth. To focus the laser beam on the metallic sheet, a plano-convex spherical lens with a focal length of 2 cm is used.

Experimental Data and Analysis

First Experiment: Determining a Transmission Spectral Map Response and a Reflection Spectral Map Response of the Biosensor 100

During the simulation of the biosensor 100, the transmission spectral map response and the reflection spectral map response of the biosensor 100 were analyzed with different asymmetrical geometrical configurations.

Figures 2A, 2B:
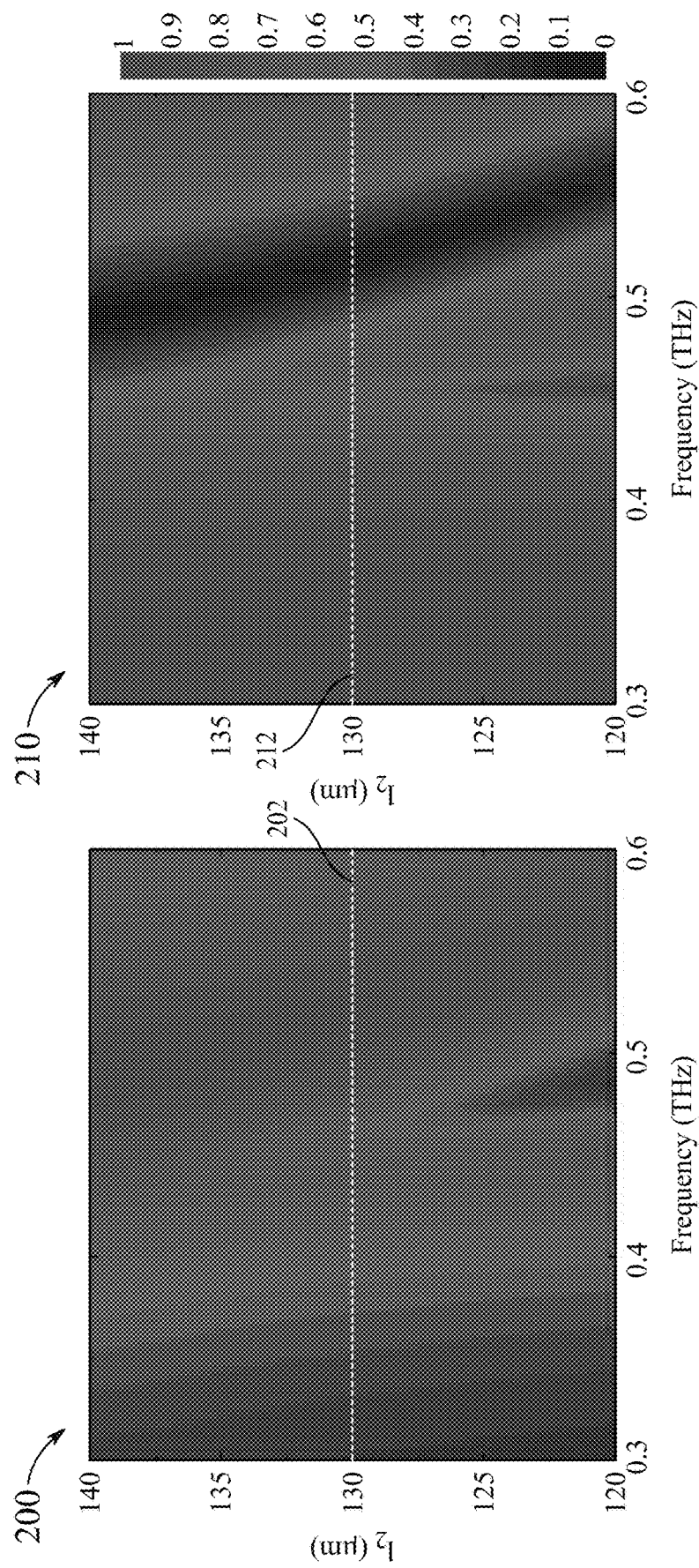
FIG. 2A is a graph of a transmission spectral map response of the biosensor, according to certain embodiments.
FIG. 2B is a graph of a reflection spectral map response of the biosensor, according to certain embodiments.

FIG. 2A is a graph 200 of the transmission spectral map response of the biosensor 100. FIG. 2A displays the transmission spectral map response (transmission amplitude spectral response) for the biosensor 100, when the terahertz radiation was swept over the biosensor in a normal direction for values of the length $l_2$ of the second arm 118 ranging between 120 μm and 140 μm with a step of 1 μm. In order to investigate the performance of the biosensor 100, a value of $l_2$=130 μm was selected as indicated by the dotted white line (202) as shown in FIG. 2A. In FIG. 2A, the changes in shading represent changes in the transmitted light intensity.

FIG. 2B is a graph 210 of the reflection spectral map response of the biosensor 100. FIG. 2B displays the reflection spectral map response (reflection amplitude spectral response) for the biosensor 100, when the terahertz radiation swept through the second arm 118 having the length $l_2$ between 120 μm and 140 μm with a step of 1 μm. A value of $l_2$=130 μm was selected to determine the performance of the biosensor, as indicated by the dotted white line (212) in FIG. 2B. In FIG. 2B, the changes in shading represent changes in the reflected light intensity.

As shown in FIG. 2A-FIG. 2B, when the lengths of the first arm 116 and the second arm are equal, i.e., $l_2$=$l_1$=140 μm, the structure of the biosensor 100 is completely symmetric and hence only the dipole resonance (symmetric resonance) is achieved. This can be seen by the dip in the response between 0.5 THz and 0.55 THz. The symmetric resonance is presented by a broad response with a peak in the transmission spectral map response and a dip in the reflection spectral map response as shown in FIG. 2A-FIG. 2B, respectively. When the lengths of the first arm 116 and the second arm 118 are unequal, the dip in the response shifted to the right. For example, the dip in the response for $l_2$=120 μm shifted to between 0.55 THz and 0.58 THz. This redshift is directly related to the glucose concentration of the sample. Second Experiment: Determining a transmission frequency response and a reflection frequency response of the biosensor 100.

During the simulation of the biosensor 100, the transmission frequency response and the reflection frequency response of the biosensor 100 were studied with different asymmetrical geometrical configurations.

Figure 3A:
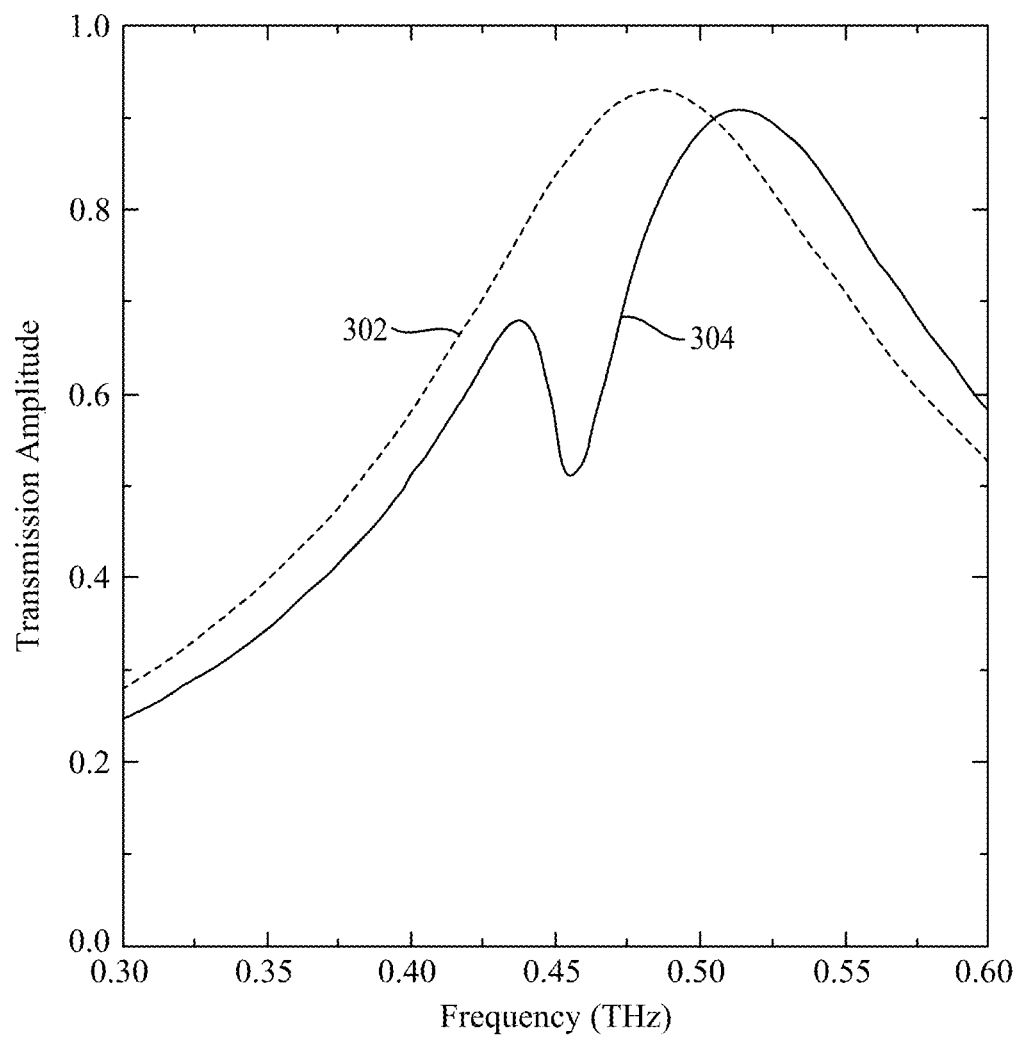
FIG. 3A is a graph of transmission frequency response of the biosensor for a symmetric configuration when $l_2$=140 μm and for an asymmetric configuration when $l_2$=130 μm, according to certain embodiments.

FIG. 3A is a graph 300 of the transmission frequency response of the biosensor 100 for a symmetric configuration (a configuration where $l_1$=$l_2$) when $l_2$=140 μm, and for an asymmetric configuration (a configuration where $l_1$ is not equal to $l_2$) when $l_2$=130 μm. Curve 302 represents the transmission frequency response for the symmetric configuration. Curve 304 represents the transmission frequency response for the asymmetric configuration.

Figure 3B:
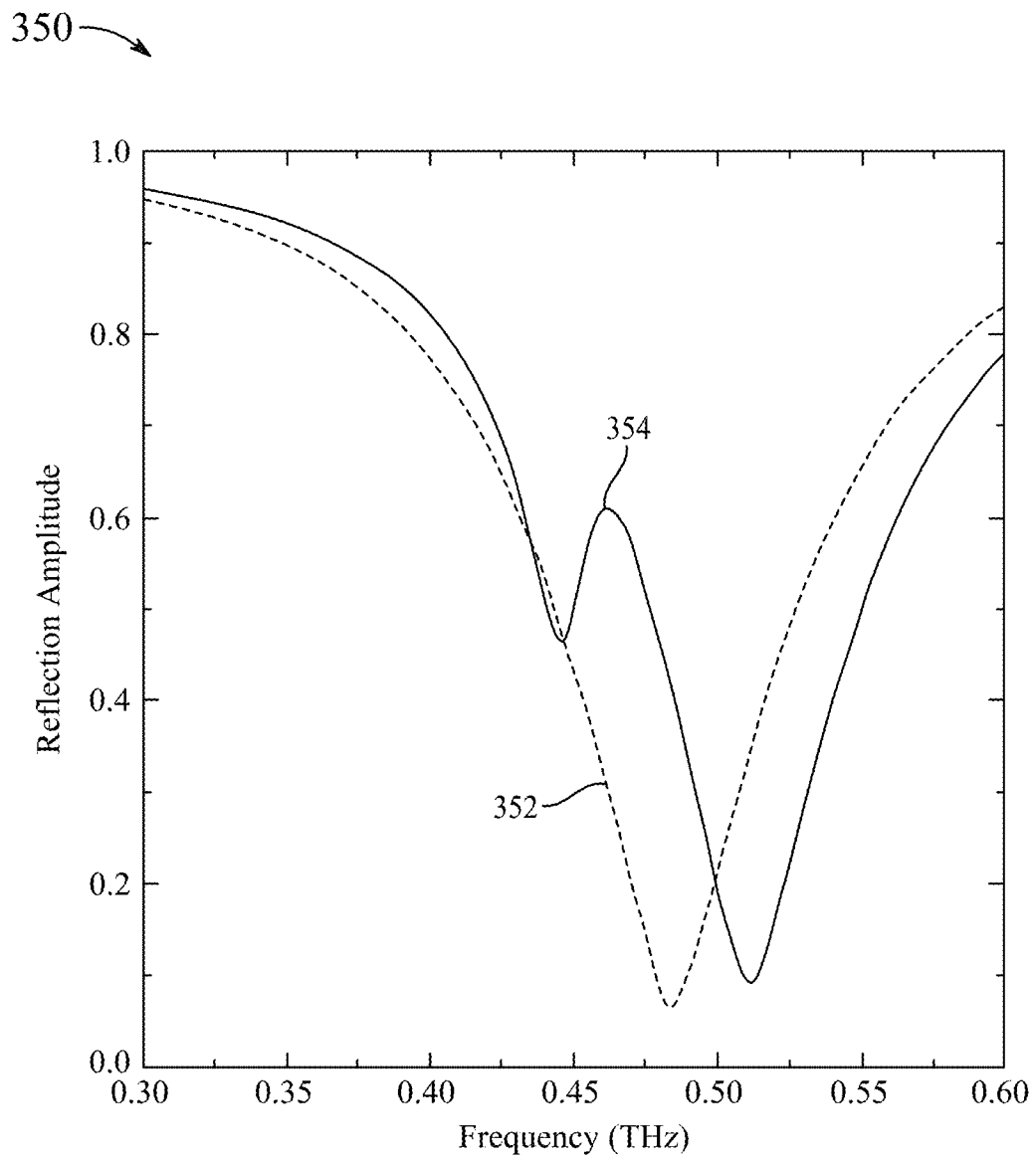
FIG. 3B is a graph of a reflection frequency response of the biosensor for the symmetric configuration when $l_2$=140 μm and for an asymmetric configuration when $l_2$=130 μm, according to certain embodiments.

FIG. 3B is a graph 350 of the reflection frequency response of the biosensor 100 for the symmetric configuration and for the asymmetric configuration. Curve 352 represents the reflection frequency response for the symmetric configuration when $l_2$=140 μm. Curve 354 represents the reflection frequency response for the asymmetric configuration when $l_2$=130 μm. The spectral response of the symmetric configuration is also shown by the dotted lines (302, 352) in FIG. 3A-FIG. 3B.

During experimentation, a dipole resonance frequency dip in the reflection amplitude was excited at 0.484 THz and is symmetric with a broad spectral response, as shown in FIG. 3A-FIG. 3B. The symmetric configuration also corresponds to symmetry-protected bound states in the continuum (BIC) state. Once the dimension l2 is decreased, the structure becomes asymmetric, and a small amplitude asymmetric resonance is excited that becomes visible in FIG. 2A-FIG. 2B when $l_2$=135 μm. A symmetry breaking allows the radiation of an asymmetric resonance mode into the far field. The asymmetric resonance mode is also called Fano-like resonance, which is a special case of BIC called quasi-BIC. The peak in the transmission amplitude was shifted gradually as well as the dip in the reflection amplitude as a result of modifying the electrical length of the two arms (the first arm 116, and the second arm 118) of the resonator. Further decreasing $l_2$ leads to broadening of the asymmetric resonance and its spectral bandwidth. Hence, the quality (Q) factor, which is defined as the ratio of resonance frequency to the bandwidth, was decreased. A small Q-factor is correlated with a low field confinement and, hence, less field-sample interaction. In order to investigate the performance of the biosensor 100, the value of $l_2$=130 μm was selected as indicated by the dotted lines (202, 212) shown in FIG. 2A-FIG. 2B. The exact transmission spectral response and the reflection spectral response for this configuration (when $l_2$=130 μm) is shown in FIG. 3A-FIG. 3B as solid lines (302, 352) with a clear asymmetric resonance in line 304 and 354 respectively. The asymmetric resonance dip in the reflection response was excited at 0.446 THz as shown in FIG. 3B. This configuration (when $l_2$=130 μm) was adopted for all the analyses discussed below. FIG. 3A-FIG. 3B, represent a trade-off between the amplitude of the resonance and its sharpness in order to facilitate reliable measurements for a practical dynamic range of the THz spectrometers that are available and the measurable scan time window.

Third Experiment: Analysis of the Electric Field Spatial Distributions

To obtain an understanding of the resonance excitation, additional simulations to visualize the electromagnetic fields were carried out for both symmetric and asymmetric resonance frequencies as shown in FIG. 4A-FIG. 4D when $l_2$=130 μm. FIG. 4A-FIG. 4D represent the spatial distributions of electric field (E) and magnetic (H) field at the surface of the structure for the Fano-like asymmetric resonance and symmetric dipole resonance modes.

Figure 4A:
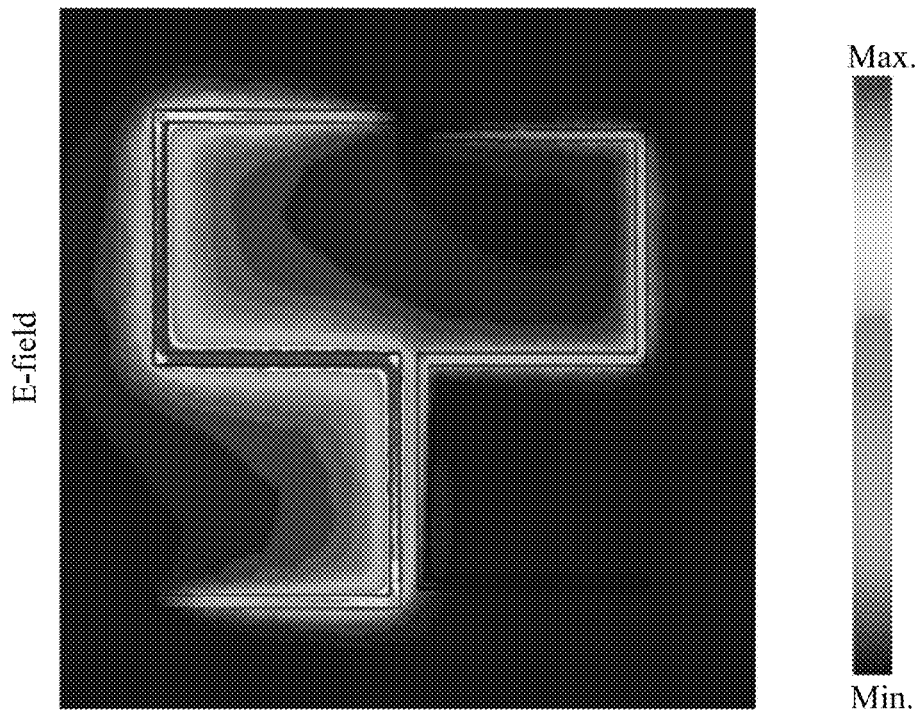
FIG. 4A is a representation of spatial distributions of electric fields at a surface of a metasurface for an asymmetric resonance mode, according to certain embodiments.
Figure 4B:
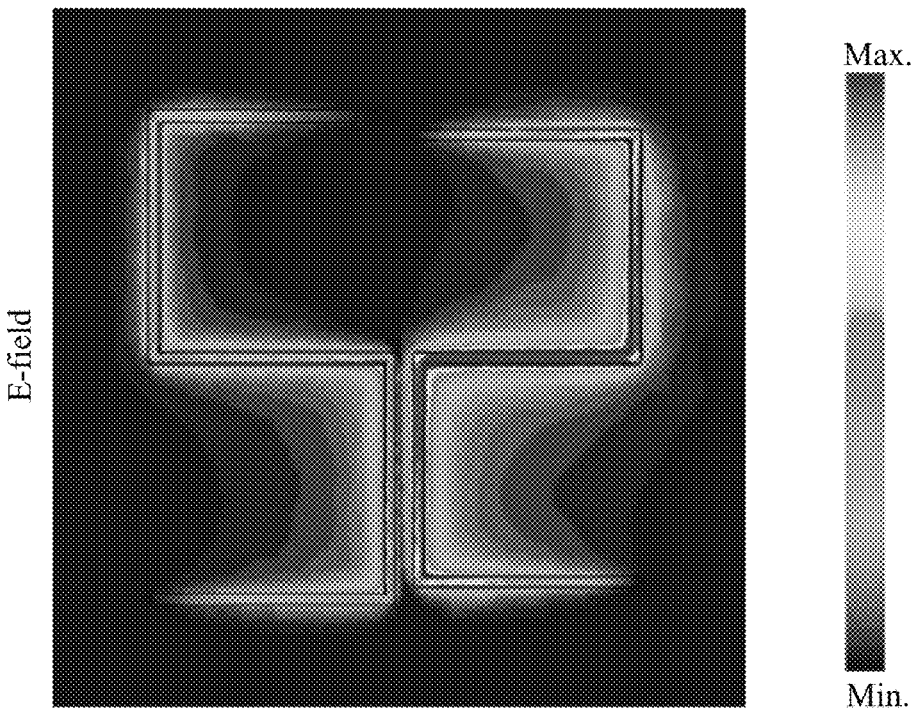
FIG. 4B is a representation of the spatial distributions of electric fields at the surface of the metasurface for a symmetric dipole resonance mode, according to certain embodiments.
Figure 4C:
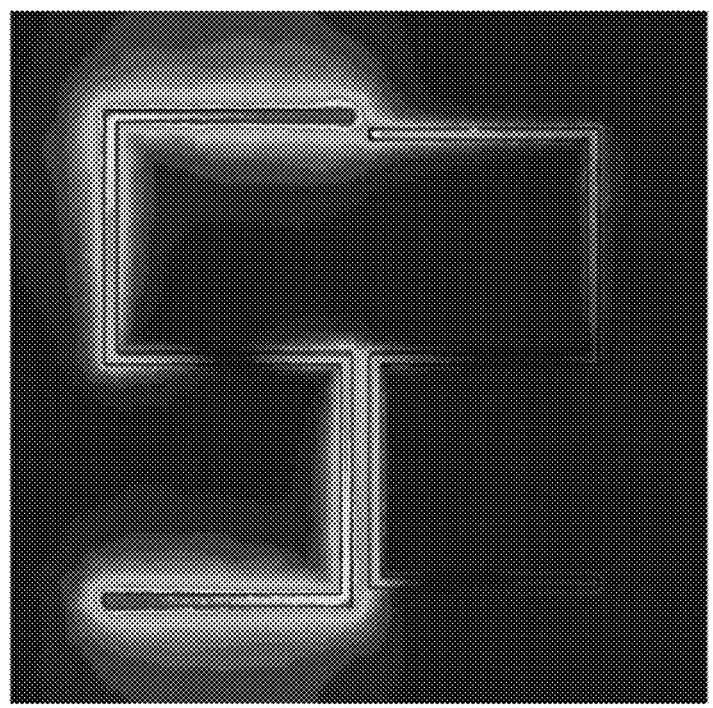
FIG. 4C is a representation of the spatial distributions of magnetic fields at the surface of the metasurface for the asymmetric resonance mode, according to certain embodiments.
Figure 4D:
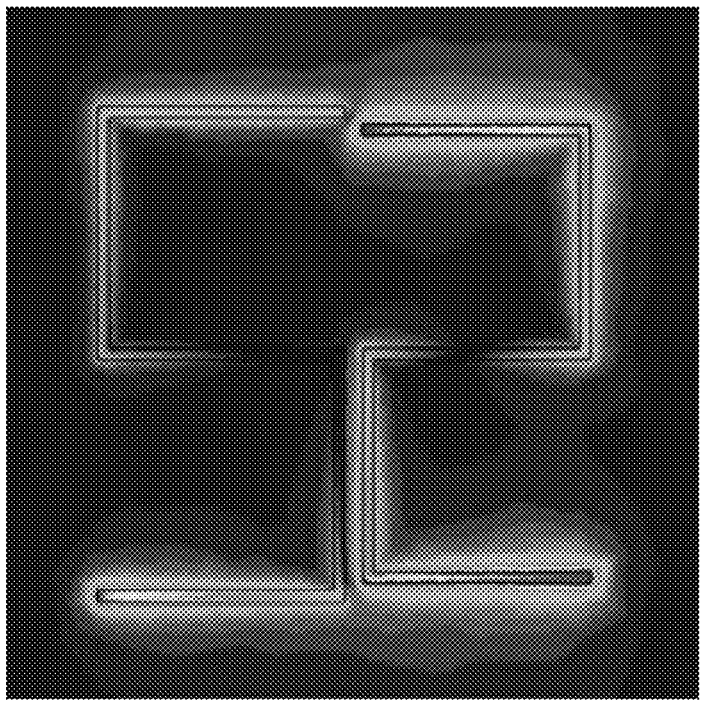
FIG. 4D is a representation of the spatial distributions of magnetic fields at the surface of the metasurface for the symmetric dipole resonance mode, according to certain embodiments.

FIG. 4A is a representation 400 of the spatial distributions of electric fields at the surface of the metasurface 100 for the asymmetric resonance mode. FIG. 4B is a representation 410 of the spatial distributions of electric fields at the surface of the metasurface 100 for the symmetric resonance mode. FIG. 4C is a representation 420 of the spatial distributions of magnetic fields at the surface of the metasurface 100 for the asymmetric resonance mode. FIG. 4D is a representation 430 of the spatial distributions of magnetic fields at the surface of the metasurface 100 for the symmetric resonance mode.

From FIG. 4A-FIG. 4D, it is evident that the electric filed (E-field) and the magnetic field (H-field) complement each other in terms of excitation location. For example, the E-field displayed in FIG. 4A is confined and maximum in the vertical slots as well as the horizontal middle slot of the first arm 116 (left arm) for the asymmetric mode. However, the H-field as shown in FIG. 4C, is confined and maximum in the upper and lower horizontal slots of the first arm 116. Similar observations were made for the symmetric mode shown in FIG. 4B and FIG. 4D for the electric field and the magnetic field, respectively. It is evident that both arms (the first arm 116 and the right arm 118) were excited in the symmetric mode. The excitation in the second arm 118 (right arm) was higher as compared to the first arm 116 as the first arm 116 represents a smaller electrical length and is hence related to the higher frequency of the symmetric resonance mode compared to the asymmetric resonance mode. Visualizing the fields not only helps in understanding the behavior of the biosensor 100 (resonator) but also helps in using a smaller quantity of analyte to coat some locations only where the field is highly confined. Based on the above, the THz wave-sample interaction was defined, and it was determined that the achieved sensitivity can be as good as covering the whole structure, but with a smaller amount of sample material.

Fourth Experiment: Analyzing the Response of the Biosensor 100 to Different Glucose Concentrations In order to measure a wide range of glucose levels from a hypoglycemia condition to a hyperglycemia condition, the responses of the biosensor 100 with respect to different glucose concentrations were analyzed. Further, the response of the biosensor 100 when either the front surface or both surfaces (the front surface and the back surface) covered for different sample thicknesses were also analyzed. A wavelength sensitivity of the biosensor 100 was also examined by simulating different settings with a range of the refractive index of the sample layers (analyte layers).

The performance of the biosensor 100 for different glucose samples with various glucose concentration levels was examined. In an example, the biosensor 100 is configured to cover hypoglycemia, normal, and hyperglycemia conditions of a diabetic from 54 mg/dL to 342 mg/dL. As the glucose sample with each concentration level has a unique dielectric constant value, the dielectric environment of the metasurface is also modified, resulting in the redshift in the resonance frequency.

In the present disclosure, two scenarios were considered:
(i) the glucose sample is applied on the front surface of the metasurface only, and
(ii) the metasurface is immersed in the glucose sample, i.e., such that the top surface and the back surface of the metasurface is covered with the glucose sample as shown in FIG. 1B.

In both scenarios, the sample thickness of each sample layer was swept from 2 μm to 20 μm. Therefore, there may be a minimum and a maximum redshift in the resonance frequency when the sample thickness is 2 μm for a glucose concentration level of 54 mg/dL and when the sample thickness is 20 μm for the glucose concentration level of 342 mg/dL, respectively. The results of the two scenarios are presented in FIG. 5A, and FIG. 5B, respectively.

Figure 5A:
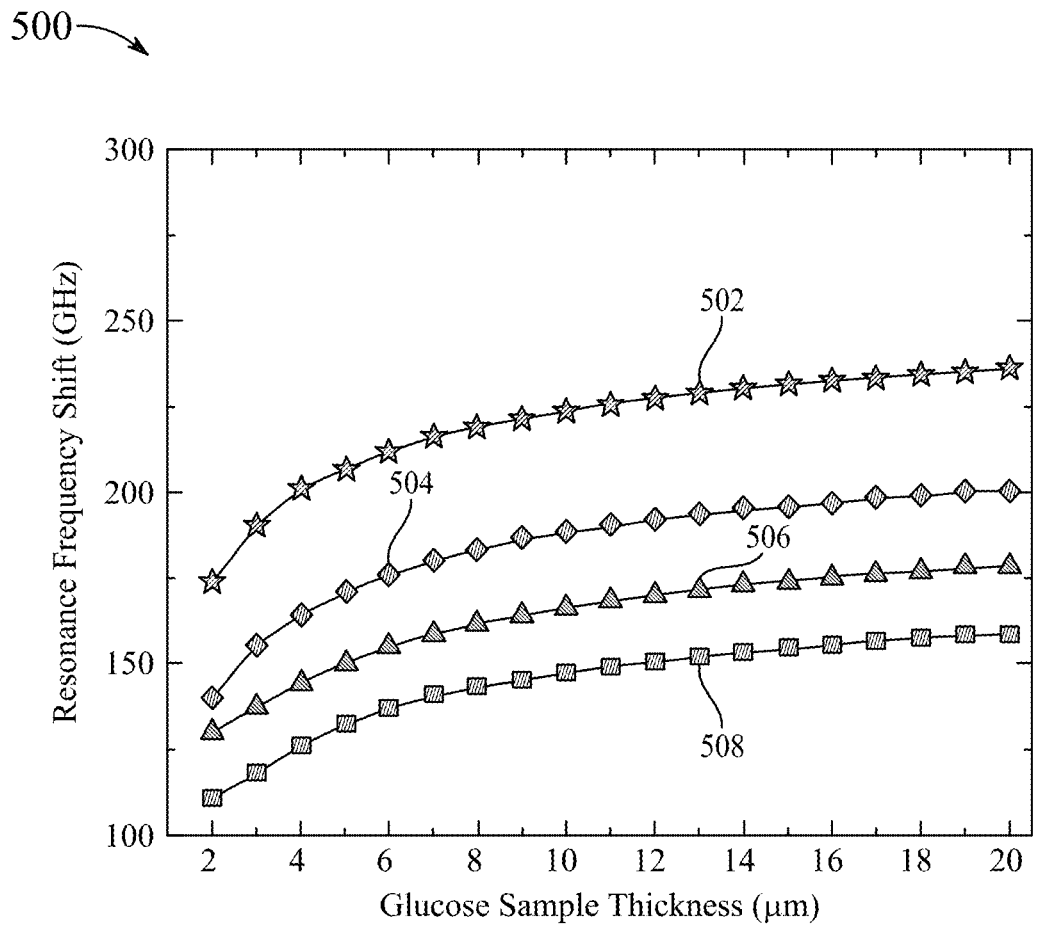
FIG. 5A is a representation of the asymmetric resonance frequency shifts when a front surface of the biosensor is considered for different glucose concentration levels, according to certain embodiments.

FIG. 5A is a representation 500 of an asymmetric resonance frequency shifts when the front surface of the biosensor 100 is considered for different glucose concentration levels. Curve 502 indicates the resonance frequency shift when the glucose concentration level is 342 mg/dL. Curve 504 represents the resonance frequency shift when the glucose concentration level is 268.2 mg/dL. Curve 506 represents the resonance frequency shift when the glucose concentration level is 111.6 mg/dL. Curve 508 represents the resonance frequency shift when the glucose concentration level is 54 mg/dL.

Figure 5B:
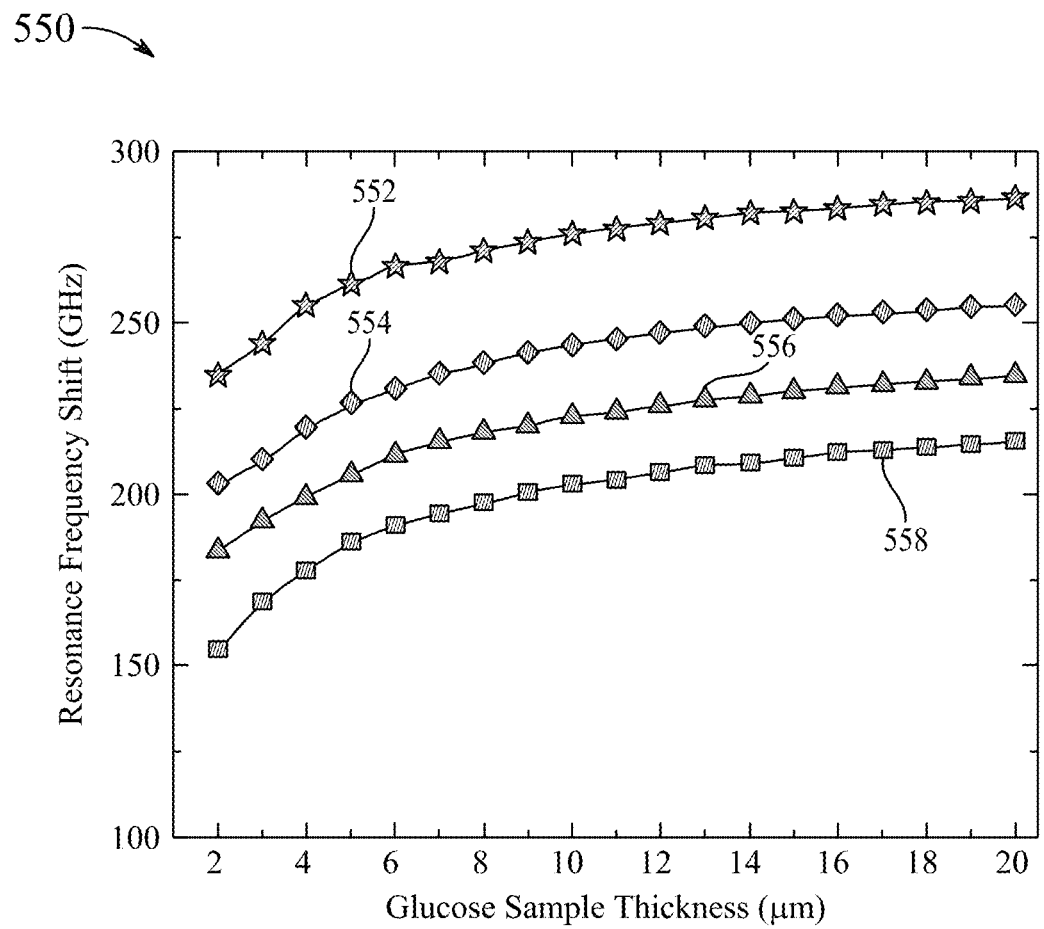
FIG. 5B is a representation of the asymmetric resonance frequency shifts when the front surface and a back surface of the biosensor are considered for different glucose concentration levels, according to certain embodiments.

FIG. 5B is a representation 550 of the asymmetric resonance frequency shifts when the front surface and the back surface of the biosensor 100 are considered for different glucose concentration levels. Curve 552 represents the resonance frequency shift when the glucose concentration level is 342 mg/dL. Curve 554 represents the resonance frequency shift when the glucose concentration level is 268.2 mg/dL. Curve 556 represents the resonance frequency shift when the glucose concentration level is 111.6 mg/dL. Curve 558 represents the resonance frequency shift when the glucose concentration level is 54 mg/dL.

An observation was made from FIG. 5A that even with the sample thickness of 2 μm and the glucose concentration level of 54 mg/dL, there is a significant redshift of 110.6 GHz. The corresponding redshift with 20 μm sample thickness and the glucose concentration level of 342 mg/dL is 236.1 GHz. FIG. 5A-FIG. 5B show that the biosensor 100 is configured to measure a small amount of the glucose sample with small glucose concentration levels, thereby covering the hypoglycemia range. Increasing the thickness of the sample layer and hence the amount of the sample as presented in FIG. 5A leads to an increase in the redshift of the asymmetric resonance mode. Different concentration levels such as 111.6 mg/dL, 268.2 mg/dL, and 342 mg/dL show a distinct frequency shift and hence can be observed from each other easily.

FIG. 5A-FIG. 5B show that the redshift starts to a saturate beyond the sample thickness of 10 µm. FIG. 5B, when the top surface and the back surfaces are covered, reveals a clear improvement in the performance of the biosensor 100 as the resonance frequency shift is larger as compared with FIG. 5A (when the front surface is covered only). The redshift with 20 µm sample thickness and the glucose concentration level of 342 mg/dL reaches 286.6 GHz. These results reveal an important advantage of the biosensor as the biosensor 100 can be immersed in the glucose sample. To implement such a scenario experimentally, a cuvette is required. In an example, the cuvette has a thickness in a propagation direction equal to a thickness of the top surface and the back surfaces. The freestanding metasurface can be placed in the middle of such cuvette.

Fifth Experiment: Assessing the Sensing Capability of the Biosensor 100

During experimentation, a conventional assessment of the sensing capability (to remove the effects of scattering) was performed. During the conventional assessment of the sensing capability, a glucose sample of the maximum thickness of 20 µm was considered with a range of refractive index between 1.2 and 2.0.

Figure 6:
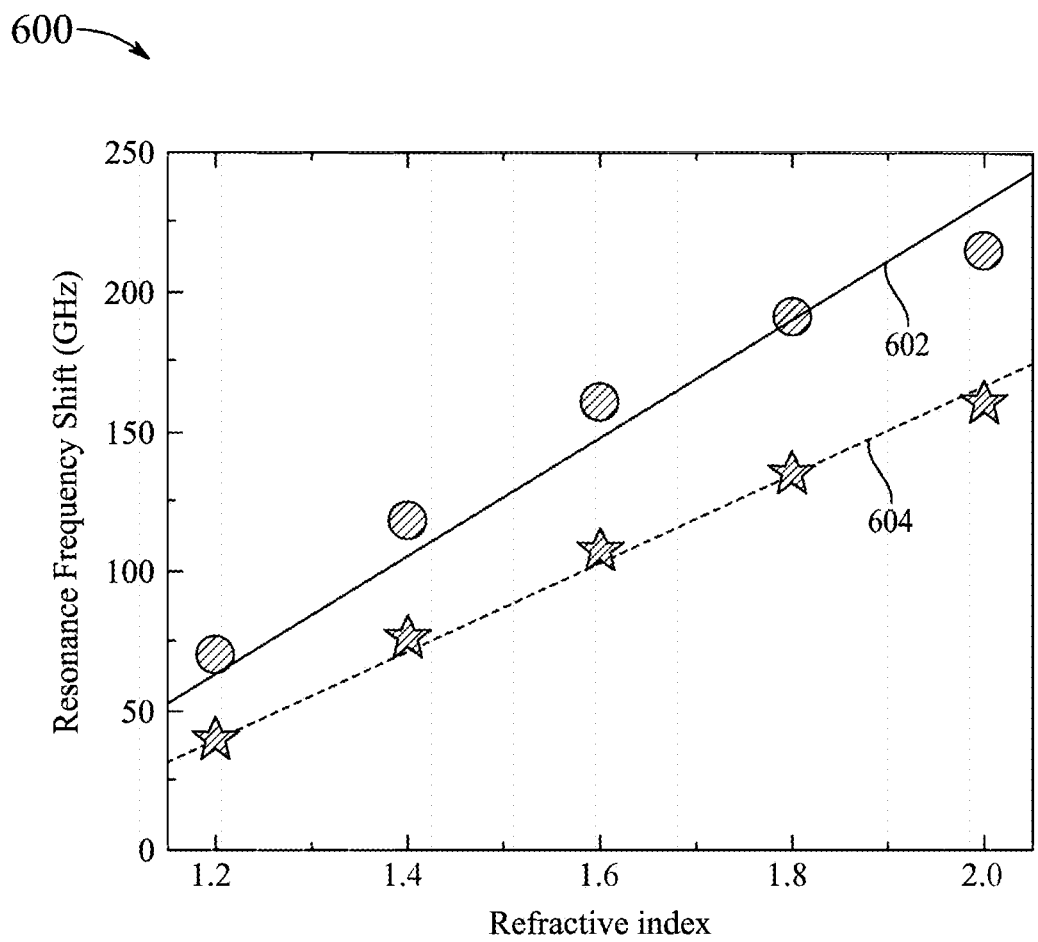
FIG. 6 is a representation of the asymmetric resonance frequency shifts for the front surface of the biosensor and for both the front surface and back surface of the biosensor for different values of the refractive index between 1.2 and 2.0, according to certain embodiments.

FIG. 6 is a representation 600 of the asymmetric resonance frequency shifts in two scenarios. In the first scenario (a front surface scenario), the front surface of the biosensor 100 was considered. In the second scenario, both the front surface and back surface of the biosensor 100 were considered for the glucose sample of the maximum thickness of 20 µm having different refractive index value in a range of between 1.2 and 2.0. A metric of design sensitivity was developed that measured a slope of the fitting lines of the resonance frequency shift in GHz per refractive index unit (RIU). As the slope of the fitting lines increased, it became easier to differentiate between two glucose analytes having close glucose concentration levels. Hence, it was determined to increase the slope of the fitting lines. Curve 604 illustrates the asymmetric resonance frequency shifts when the front surface of the biosensor 100 is considered. The front surface scenario resulted a fitting line with a slope of 160 GHz/RIU. Curve 602 illustrates the asymmetric resonance frequency shifts when the second scenario is considered. In the second scenario, a fitting line with a slope of 214 GHz/RIU is achieved. As shown in FIG. 6, line 602 is larger than the line 604, therefore the second scenario is advantageous over the front surface scenario, as it indicated higher sensitivity.

However, the slope can increase or decrease if the exact resonance frequency is larger or smaller than the one of the current design, respectively. Therefore, a comprehensive approach was to use the wavelength sensitivity, which is calculated using the following relation:

$$S = \left|\frac{d\lambda}{dn}\right| = \frac{\Delta f}{\Delta n} \times \frac{c_o}{f_r^2}, \quad (1)$$

where $\Delta f$ is the asymmetric resonance frequency shift, $\Delta n$ is the difference in the refractive index, co is the speed of light in free space, and $f_r$ is the resonance frequency.

Calculating the sensing capability (sensitivity) using the equation (1) offers a fair assessment as the resonance frequency is considered in the equation (1). The sensitivity analysis showed a high sensitivity level of 241,308 nm/RIU for the first scenario and 322,749 nm/RIU for the biosensor 100 for the second scenario. Simulating the biosensor 100 with an overlayer thickness of 20 µm revealed a wavelength sensitivity of 140,000 nm/RIU. For a proper comparison among different configurations and biosensors, it is required to consider at least ten different parameters (See: Ibraheem Al-Naib, "*Sensing glucose concentration using symmetric metasurfaces under oblique incident terahertz waves*", Crystals 2021, 11, incorporated herein by reference in its entirety). In the present disclosure, the biosensor 100 has three main aspects:

(i) freestanding structure, therefore, can be easily fabricated.
(ii) working under normal incidence, enabling a simple measurement configuration and procedure.
iii) offering high wavelength sensitivity.

Hence, excellent performance of the biosensor 100 can be achieved with the simple fabrication process and a conventional experimental setup based on the transmission mode configuration. In an example, the quasi-BIC of the present disclosure is in the geometry space.

Figure 7:
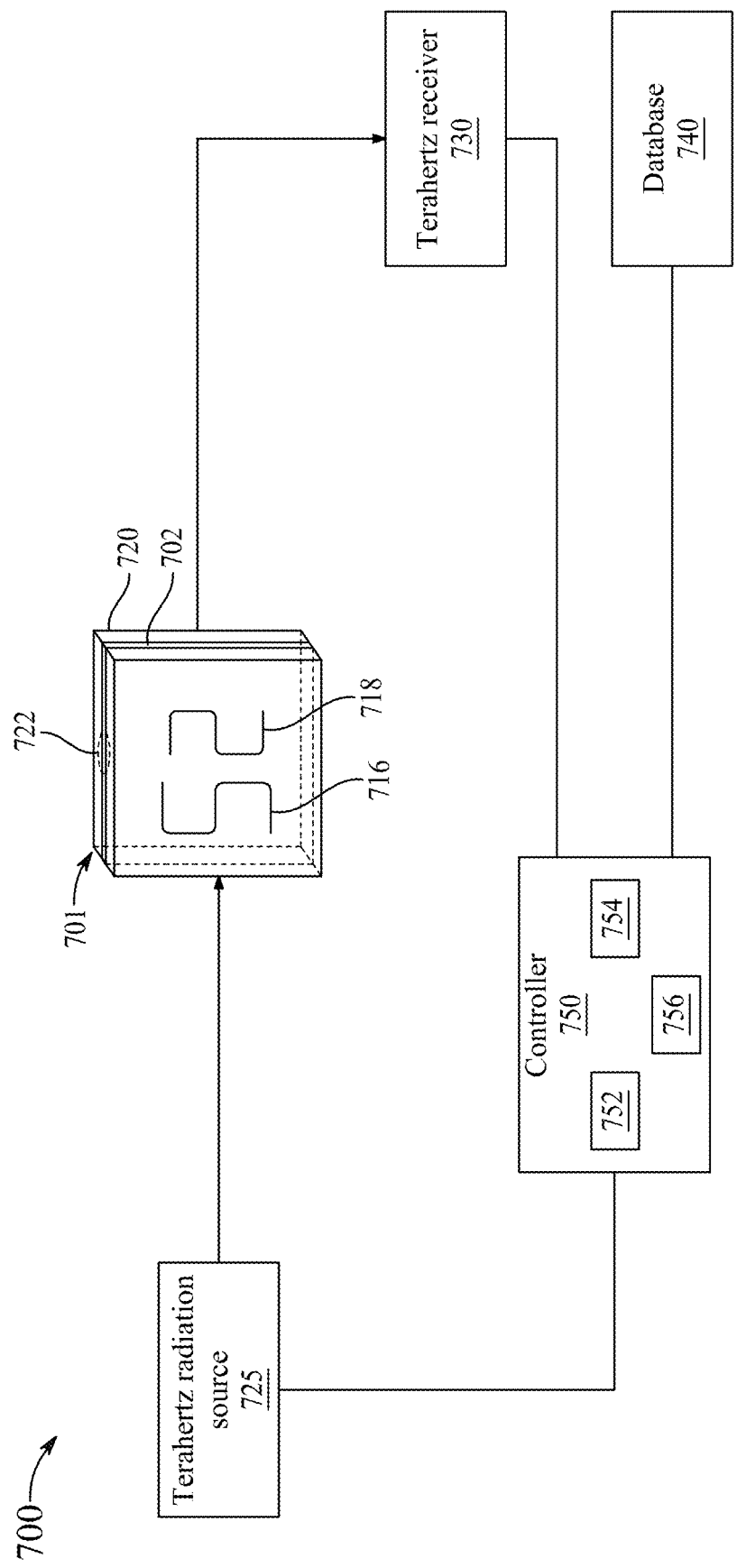
FIG. 7 is an exemplary illustration of a system for measuring glucose concentration of an analyte, according to certain embodiments.

FIG. 7 is an exemplary illustration of a system 700 for measuring glucose concentration of an analyte (hereinafter interchangeably referred to as "the system 700"), according to one or more aspects of the present disclosure. The system 700 includes an asymmetric S-shaped complementary metasurface biosensor 701, a terahertz radiation source 725, a terahertz receiver 730, a database 740, and a controller 750.

The basic construction of the asymmetric S-shaped complementary metasurface biosensor 701 is the same as that of the biosensor 100, and thus the construction is not explained in detail for the sake of brevity. The biosensor 701 includes a metallic sheet 702, a first arm 716, and a second arm 718 separated by a gap g. In an aspect, the gap g is 3 µm wide. The metallic sheet 702 is configured to receive a glucose sample. In an aspect, the metallic sheet 702 is one of an aluminum sheet, a gold sheet, a graphene sheet and a silver sheet.

The first arm 716 is configured as an S-shaped slot in the metallic sheet 702. The first arm 716 has a length $l_1$ and a width equal to one half of the length $l_1$ (as shown in FIG. 1A). The second arm 718 is spaced apart from the first arm 716 by a gap g. The second arm is configured to be an S-shaped slot in the metallic sheet 702 which is a mirror image of the first arm. The second arm has a length $l_2$. In an example, the length $l_2$ is equal to $l_1$–d. The value of d ranges from about 1% of $l_1$ to about 15% of $l_1$, and to have a width equal to one half of the length $l_2$.

In an aspect, the asymmetric S-shaped complementary metasurface biosensor 701 includes a transparent casing 720, and an opening 722 located in the transparent casing. The transparent casing 720 is configured to hold the metallic sheet 702. The opening 722 is configured to receive the glucose sample. The opening is shown at the top of 701 but may be configured as an open window directly above the S-shaped slots 716 and 718. The transparent casing 720 is configured such that the glucose sample coats at least one of the front surface and the back surface of the metallic sheet 702. The transparent casing 720 is configured to rigidly hold the metallic sheet to prevent buckling of the S-shaped arms and thus distortion of the resonance response. In the example in which the biosensor 701 is inserted into a cuvette holding the glucose sample, there may be an open window at both the front side and the back side of casing to allow contact with the glucose sample. Alternatively, the opening 722 as shown in FIG. 7 may include a front internal capillary and a back internal capillary which draws the glucose sample into the casing and distributes it to the front and the back. In the aspect in which only the front side contacts the sample, the opening 722 may include a front internal capillary which draws the glucose sample into the casing and distributes it to the front side of the S-shaped arms 716 and 718. The S-shaped arms 716 and 718 may be configured to be filled with the glucose sample, in which case the capillary(s) may be connected to the ends of the S-shaped arms. Alternatively, the glucose sample may be drawn into the casing and be evenly distributed over the metallic surface. The casing may be a cuvette which is transparent to the terahertz waves.

The terahertz radiation source 725 is configured to generate a range of frequencies. The terahertz radiation source 725 is configured to sweep a terahertz radiation beam at the range of frequencies across the metallic sheet 702 in a direction normal to the front side of the metallic sheet such that the first arm 716 resonates at a first resonant frequency and the second arm resonates at a second resonant frequency. In an example, terahertz radiation source 725 is selected from the group includes a broadband spectral lamp, a gas laser, a solid-state laser, a free electron laser and an ultra-high frequency electronic generator.

The terahertz receiver 730 is configured to receive light beams reflected from and/or transmitted through the first arm 716 and the second arm. Based on the received light beams, the terahertz receiver 730 is configured to generate electrical signals indicative of a redshift of the resonance when the analyte is applied to the metallic surface.

The database 740 includes records relating the redshift to glucose concentration in the analyte. For a given glucose sample, the concentration is fixed. Hence, there is no direct relationship between the resonance frequency and the concentration of the glucose sample. However, the redshift in the resonance frequency is used as a measure for the concentration of the glucose sample.

The controller 750 is operatively connected to the terahertz radiation source 725, the terahertz radiation receiver, and the database 740. The controller 750 has a circuitry 752, a memory 754 holding program instructions, and at least one processor 756.

The circuitry 752 is configured to employ preprocessing on the received data, such as filtering and amplifying the received data.

The memory 754 is configured to store the preprocessed data and the program instructions. The memory 754 is configured to store a plurality of reflection frequency responses, a plurality of transmission frequency responses, a plurality of resonance frequency shift values, and the like. The memory 754 may include any computer-readable medium known in the art including, for example, volatile memory, such as Static Random Access Memory (SRAM) and Dynamic Random Access Memory (DRAM) and/or nonvolatile memory, such as Read Only Memory (ROM), erasable programmable ROM, flash memories, hard disks, optical disks, and magnetic tapes.

The at least one processor 756 is configured to fetch and execute computer-readable program instructions stored in the memory 754. The at least one processor 756 is configured to execute a sequence of machine-readable instructions, which may be embodied in a program or software. The instructions can be directed to the processor 756, which may subsequently program or otherwise be configured to implement the methods of the present disclosure. In some examples, the processor 756 is configured to control and/or communicate with large databases, perform high-volume transaction processing, and generate reports from large databases. The at least one processor 756 may be implemented as one or more microprocessors, microcomputers, microcontrollers, digital signal processors, central processing units, state machines, logic circuitries, and/or any devices that manipulate signals based on operational instructions.

Under the execution of the program instructions, the at least one processor 756 is configured to activate the terahertz radiation source 725 to project the terahertz radiation beam at the range of frequencies onto the metallic sheet 702. Under the execution of the program instructions, the at least one processor 756 is configured to receive the electrical signals from the terahertz receiver 730. Under the execution of the program instructions, the at least one processor 756 is configured to match the redshift to a record in the database 740 which identifies the glucose concentration of the analyte.

The present disclosure describes a free-standing terahertz metasurface 100 based on asymmetric S-shaped complementary resonators under normal incidence in transmission mode configuration. Each unit cell of the metasurface 100 includes two arms of mirrored S-shaped slots. During the experimentation, the frequency response for different geometrical asymmetries via modifying the dimensions of one arm of the resonator was analyzed. The present configuration enables an excitation of asymmetric quasi-bound states in the continuum resonance and, hence, features field confinement that is critical for biosensing applications. Moreover, the performance of the present configuration as a biosensor was examined for glucose concentration levels from 54 mg/dL to 342 mg/dL. This range covers hypoglycemia, normal, and hyperglycemia diabetes mellitus conditions. In the present disclosure, two sample coating scenarios were considered. The first scenario is to have the sample cover the front surface of the metasurface, and the second scenario is to have metasurface sandwiched between the two layers of analyte. The two sample coating approach enables large resonance frequency redshifts of 236.1 GHz and 286.6 GHz that were observed for the two scenarios for a 342 mg/dL concentration level and a layer thickness of 20 µm. Furthermore, for the second scenario and the same thickness, a wavelength sensitivity of 322,749 nm/RIU was found, which represents a factor of 2.3 enhancement compared to previous case. The terahertz metasurface biosensor may be used for identifying hypoglycemia and hyperglycemia conditions.

In an aspect, the biosensor 100 can be utilized for any other sample (including thin layers of semiconductors).

The first embodiment is illustrated with respect to FIG. 1A-FIG. 1B. The first embodiment describes the asymmetric S-shaped complementary metasurface biosensor 100 for sensing glucose concentration. The biosensor includes a metallic sheet 102, a first arm 116, and a second arm 118. The metallic sheet 102 is configured to receive a glucose sample. The first arm 116 is configured as an S-shaped slot in the metallic sheet 102. The first arm 116 is configured to have a length $l_1$ and a width equal to one half of the length $l_1$. The second arm is spaced apart from the first arm 116 by a gap g. The second arm 118 is configured as an S-shaped slot in the metallic sheet 102 which is a mirror image of the first arm. The second arm 118 is configured to have a length $l_2$. The length $l_2 = l_1 - d$, where d ranges from about 1% of $l_1$ to about 15% of $l_1$. The first arm and the second arm are configured to resonate at an asymmetric resonant frequency when a terahertz radiation is swept in a direction normal to the metallic sheet, wherein a redshift in the asymmetric resonant frequency is indicative of a glucose concentration in the glucose sample.

In an aspect, a width of the slot is about 3 microns; the length $l_1$ is about 140 microns; the length $l_2$ is selected from a range of about 120 microns to about 139 microns; the gap is about 4.5 microns; and the metallic sheet 102 has a thickness of about 200 nanometers and is configured in a square shape having a length p of about 200 microns.

In an aspect, the metallic sheet 102 is configured to receive the glucose sample at a front surface of the metallic sheet 102.

In an aspect, the metallic sheet 102 is configured to be immersed in the glucose sample such that a front surface and a back surface of the metallic sheet 102 contact the glucose sample.

In an aspect, the biosensor 100 includes a transparent casing 120 configured to hold the metallic sheet 102; and an opening located in the transparent casing to receive the glucose sample, wherein the transparent casing is configured such that the glucose sample coats at least one of the front surface and the back surface of the metallic sheet 102.

In an aspect, the biosensor 100 includes a casing 120 configured to hold the metallic sheet 102; and an opening located in the casing, wherein the opening is configured to receive the glucose sample, wherein the casing is configured such that the glucose sample coats both the front surface and the back surface of the metallic sheet 102.

In an aspect, the metallic sheet 102 includes a first edge 104, a second edge 106 parallel to the first edge 104, a third edge 108 perpendicular to the first edge 104 and the second edge 106, a fourth edge 110 parallel to the third edge 108, a first central axis 112 extending from the first edge 104 to the second edge 106, and a second central axis 114 extending from the third edge 108 to the fourth edge 110.

In an aspect, the first arm 116 includes a first leg 116a coincident with the second central axis 114, wherein a first end of the first leg 116a is configured to begin at a distance of ½ g from the first central axis 112 and extend towards the third edge 108 for a distance of $l_1/2$; a second leg having a first end connected to a second end of the first leg 116a, wherein the second leg 116b is perpendicular to the first leg 116a, wherein the second leg 116b is configured to extend towards the first edge 104 for a distance of $l_1/2$; a third leg 116c parallel to the first leg 116a, wherein the third leg 116c has a first end connected to a second end of the second leg 116b, wherein the third leg 116c is perpendicular to the second leg 116b, wherein the third leg 116c is configured to extend towards the first central axis 112 for a distance of $l_1/2$; a fourth leg 116d having a first end connected to the first end of the first leg 116a, wherein the fourth leg 116d is perpendicular to the first leg 116a, wherein the fourth leg 116d is configured to extend towards the second edge 106 for a distance of $l_1/2$; and a fifth leg 116e parallel to the first leg 116a, wherein the fifth leg 116e has a first end connected to a second end of the fourth leg 116d, wherein the fifth leg 116e is perpendicular to the fourth leg 116d, wherein the fifth leg 116e is configured to extend towards the third edge 108 for a distance of $l_1/2$.

In an aspect, the second arm 118 includes a first leg 118a coincident with the second central axis 114, wherein a first end of the first leg 118a is configured to begin at a distance of ½ g from the first central axis 112 and extend towards the fourth edge 110 for a distance of $l_2/2$; a second leg 118b having a first end connected to a second end of the first leg 118a, wherein the second leg 118b is perpendicular to the first leg 118a, wherein the second leg 118b is configured to extend towards the first edge 104 for a distance of $l_2/2$; a third leg 116c parallel to the first leg 118a, wherein the third leg 116c has a first end connected to a second end of the second leg 118b, wherein the third leg 116c is perpendicular to the second leg 118b, wherein the third leg 116c is configured to extend towards the first central axis 112 for a distance of $l_2/2$; a fourth leg 118d having a first end connected to the first end of the first leg 118a, wherein the fourth leg 118d is perpendicular to the first leg 118a, wherein the fourth leg 118d is configured to extend towards the second edge 106 for a distance of $l_2/2$; and a fifth leg 118e parallel to the first leg 118a, wherein the fifth leg 118e has a first end connected to a second end of the fourth leg 118d, wherein the fifth leg 118e is perpendicular to the fourth leg 118d, wherein the fifth leg 118e is configured to extend towards the fourth edge 110 for a distance of $l_2/2$.

In an aspect, the metallic sheet 102 is an aluminum sheet.

In an aspect, the metallic sheet 102 is one of an aluminum sheet, a gold sheet, a graphene sheet and a silver sheet.

The second embodiment is illustrated with respect to FIG. 1A-FIG. 1B. The second embodiment describes a system 700 for measuring glucose concentration of an analyte. The system 700 includes an asymmetric S-shaped complementary metasurface biosensor, a terahertz radiation source 725, a terahertz receiver 730, a database 740, and a controller 750. The asymmetric S-shaped complementary metasurface biosensor includes a metallic sheet 702, a first arm 716, and a second arm 718. The metallic sheet 702 is configured to receive a glucose sample. The first arm 716 is configured as an S-shaped slot in the metallic sheet 102. The first arm 716 has a length $l_1$ and a width equal to one half of the length $l_1$. The second arm 718 is spaced apart from the first arm 716 by a gap g. The second arm 718 is configured to be an S-shaped slot in the metallic sheet 702 which is a mirror image of the first arm 716. The second arm has a length $l_2$, wherein the length $l_2=l_1-d$, where d ranges from about 1% of $l_1$ to about 15% of $l_1$, and to have a width equal to one half of the length $l_2$. A terahertz radiation source 725 having configured to sweep a terahertz radiation beam at the range of frequencies in a normal direction to the metallic sheet 702 such that an electromagnetic coupling between the first arm and the second arm excites an asymmetric resonance frequency response.

The terahertz receiver 730 is configured to receive light beams transmitted the asymmetric S-shaped complementary metasurface biosensor and generate electrical signals indicative of a redshift in the asymmetric resonance frequency response.

The database 740 includes records relating the redshift to glucose concentration in the analyte. The controller 750 is operatively connected to the terahertz radiation source 725. The terahertz radiation receiver, and the database 740. The controller 750 has circuitry 752, a memory 754 storing program instructions and at least one processor 756 configured to execute the program instructions to: activate the terahertz radiation source 725 to project the terahertz radiation beam at the range of frequencies onto the metallic sheet 102; receive the electrical signals from the receiver; and match the redshift to a record in the database 740 which identifies the glucose concentration of the analyte.

In an aspect, the system 700 further includes a transparent casing configured to hold the metallic sheet 702; and an opening located in the transparent casing to receive the glucose sample, wherein the transparent casing is configured such that the glucose sample coats at least one of the front surface and the back surface of the metallic sheet 702.

In an aspect, the metallic sheet 702 (102) includes a first edge 104, a second edge 106 parallel to the first edge 104, a third edge 108 perpendicular to the first edge 104 and the second edge 106, a fourth edge 110 parallel to the third edge 108, a first central axis 112 extending from the first edge 104 to the second edge 106, and a second central axis 114 extending from the third edge 108 to the fourth edge 110.

In an aspect, the first arm 116 further includes a first leg 116a coincident with the second central axis 114, wherein a first end of the first leg 116a is configured to begin at a distance of ½ g from the first central axis 112 and extend towards the third edge 108 for a distance of $l_1/2$; a second leg 116b having a first end connected to a second end of the first leg 116a, wherein the second leg 116b is perpendicular to the first leg 116a, wherein the second leg 116b is configured to extend towards the first edge 104 for a distance of $l_1/2$; a third leg 116c parallel to the first leg 116a, wherein the third leg 116c has a first end connected to a second end of the second leg 116b, wherein the third leg 116c is perpendicular to the second leg 116b, wherein the third leg 116c is configured to extend towards the first central axis 112 for a distance of $l_1/2$; a fourth leg 116d having a first end connected to the first end of the first leg 116a, wherein the fourth leg 116d is perpendicular to the first leg 116a, wherein the fourth leg 116d is configured to extend towards the second edge 106 for a distance of $l_1/2$; and a fifth leg 116e parallel to the first leg 116a, wherein the fifth leg 116e has a first end connected to a second end of the fourth leg 116d, wherein the fifth leg 116e is perpendicular to the fourth leg 116d, wherein the fifth leg 116e is configured to extend towards the third edge 108 for a distance of $l_1/2$.

In an aspect, the second arm further includes a first leg 118a coincident with the second central axis 114, wherein a first end of the first leg 118a is configured to begin at a distance of ½ g from the first central axis 112 and extend towards the fourth edge 110 for a distance of $l_2/2$; a second leg 118b having a first end connected to a second end of the first leg 118a, wherein the second leg 118b is perpendicular to the first leg 118a, wherein the second leg 118b is configured to extend towards the first edge 104 for a distance of $l_2/2$; a third leg 118c parallel to the first leg 118a, wherein the third leg 118c has a first end connected to a second end of the second leg 118b, wherein the third leg 118c is perpendicular to the second leg 118b, wherein the third leg 118c is configured to extend towards the first central axis 112 for a distance of $l_2/2$; a fourth leg 118d having a first end connected to the first end of the first leg 118a, wherein the fourth leg 118d is perpendicular to the first leg 118a, wherein the fourth leg 118d is configured to extend towards the second edge 104 for a distance of $l_2/2$; and a fifth leg 118e parallel to the first leg 118a, wherein the fifth leg 118e has a first end connected to a second end of the fourth leg 118d, wherein the fifth leg 118e is perpendicular to the fourth leg 118d, wherein the fifth leg 118e is configured to extend towards the fourth edge 110 for a distance of $l_2/2$.

In an aspect, the metallic sheet 102 is one of an aluminum sheet, a gold sheet, a graphene sheet and a silver sheet.

The third embodiment is illustrated with respect to FIG. 1A-FIG. 1B. The third embodiment describes a sensor system for determining a concentration of an analyte in a test sample. The sensor system includes an asymmetric S-shaped complementary metasurface sensor, a terahertz radiation source 725, a terahertz receiver 730, a database 740, and a controller 750. The asymmetric S-shaped complementary metasurface sensor includes a metallic sheet 102, a transparent casing, an opening, a first arm, and a second arm. The metallic sheet 102 includes a first edge 104, a second edge 106 parallel to the first edge 104, a third edge 108 perpendicular to the first edge 104 and the second edge 106, a fourth edge 110 parallel to the third edge 108, a first central axis 112 extending from the first edge 104 to the second edge 106, and a second central axis 114 extending from the third edge 108 to the fourth edge 110. The transparent casing is configured to hold the metallic sheet 102. The opening is located in the transparent casing to receive the test sample. The transparent casing is configured such that the glucose sample coats at least one of the front surface and the back surface of the metallic sheet 102. The first arm 116 is configured as an S-shaped slot in the metallic sheet 102, wherein the first arm 116 has a length $l_1$ and a width equal to one half of the length $l_1$. The second arm is spaced apart from the first arm 116 by a gap g. The second arm is configured as an S-shaped slot in the metallic sheet 102 which is a mirror image of the first arm. The second arm has a length $l_2$, wherein the length $l_2=l_1-d$, where d ranges from about 1% of $l_1$ to about 15% of $l_1$, and to have a width equal to one half of the length $l_2$. The terahertz radiation source 725 has a range of frequencies. The terahertz radiation source 725 is configured to sweep a terahertz radiation beam at the range of frequencies normal to the metallic sheet 102 such that that such that an electromagnetic coupling between the first arm and the second arm excites an asymmetric resonance frequency. The terahertz receiver 730 is configured to receive light beams transmitted through the asymmetric S-shaped complementary metasurface biosensor and generate electrical signals indicative of a redshift in the asymmetric resonance frequency.

The database 740 includes records relating the redshift to the concentration of the analyte in the test sample. The controller 750 is operatively connected to the terahertz radiation source 725, the terahertz radiation receiver, and the database 740, wherein the controller 750 has circuitry, a memory storing program instructions and at least one processor configured to execute the program instructions to: activate the terahertz radiation source 725 to project the terahertz radiation beam at the range of frequencies onto the metallic sheet 102; receive the electrical signals from the receiver; and match the redshift to a record in the database 740 which identifies the analyte concentration.

In an aspect, the first arm 116 further includes a first leg 116a coincident with the second central axis 114, wherein a first end of the first leg 116a is configured to begin at a distance of ½ g from the first central axis 112 and extend towards the third edge 108 for a distance of $l_1/2$; a second leg 116b having a first end connected to a second end of the first leg 116a, wherein the second leg 116b is perpendicular to the first leg 116a, wherein the second leg 116b is configured to extend towards the first edge 104 for a distance of $l_1/2$; a third leg 116c parallel to the first leg 116a, wherein the third leg 116c has a first end connected to a second end of the second leg 116b, wherein the third leg 116c is perpendicular to the second leg 116b, wherein the third leg 116c is configured to extend towards the first central axis 112 for a distance of $l_1/2$; a fourth leg 116d having a first end connected to the first end of the first leg 116a, wherein the fourth leg 116d is perpendicular to the first leg 116a, wherein the fourth leg 116d is configured to extend towards the second edge 106 for a distance of $l_1/2$; and a fifth leg 116e parallel to the first leg 116a, wherein the fifth leg 116e has a first end connected to a second end of the fourth leg 116d, wherein the fifth leg 116e is perpendicular to the fourth leg 116d, wherein the fifth leg 116e is configured to extend towards the third edge 108 for a distance of $l_1/2$.

In an aspect, the second arm 118 further includes a first leg 118a coincident with the second central axis 114, wherein a first end of the first leg 118a is configured to begin at a distance of ½ g from the first central axis 112 and extend towards the fourth edge 110 for a distance of $l_2/2$; a second leg 118b having a first end connected to a second end of the first leg 118a, wherein the second leg 118b is perpendicular to the first leg 118a, wherein the second leg 118b is configured to extend towards the first edge 104 for a distance of $l_2/2$; a third leg 118c parallel to the first leg 118a, wherein the third leg 118c has a first end connected to a second end of the second leg 118b, wherein the third leg 118c is perpendicular to the second leg 118b, wherein the third leg 118c is configured to extend towards the first central axis 112 for a distance of $l_2/2$; a fourth leg 118d having a first end connected to the first end of the first leg 118a, wherein the fourth leg 118d is perpendicular to the first leg 118a, wherein the fourth leg 118d is configured to extend towards the second edge 106 for a distance of $l_2/2$; and a fifth leg 118e parallel to the first leg 118a, wherein the fifth leg 118e has a first end connected to a second end of the fourth leg 118d, wherein the fifth leg 118e is perpendicular to the fourth leg 118d, wherein the fifth leg 118e is configured to extend towards the fourth edge 110 for a distance of $l_2/2$.

Next, further details of the hardware description of the computing environment of FIG. 7 according to exemplary embodiments is described with reference to FIG. 8.

Figure 8:
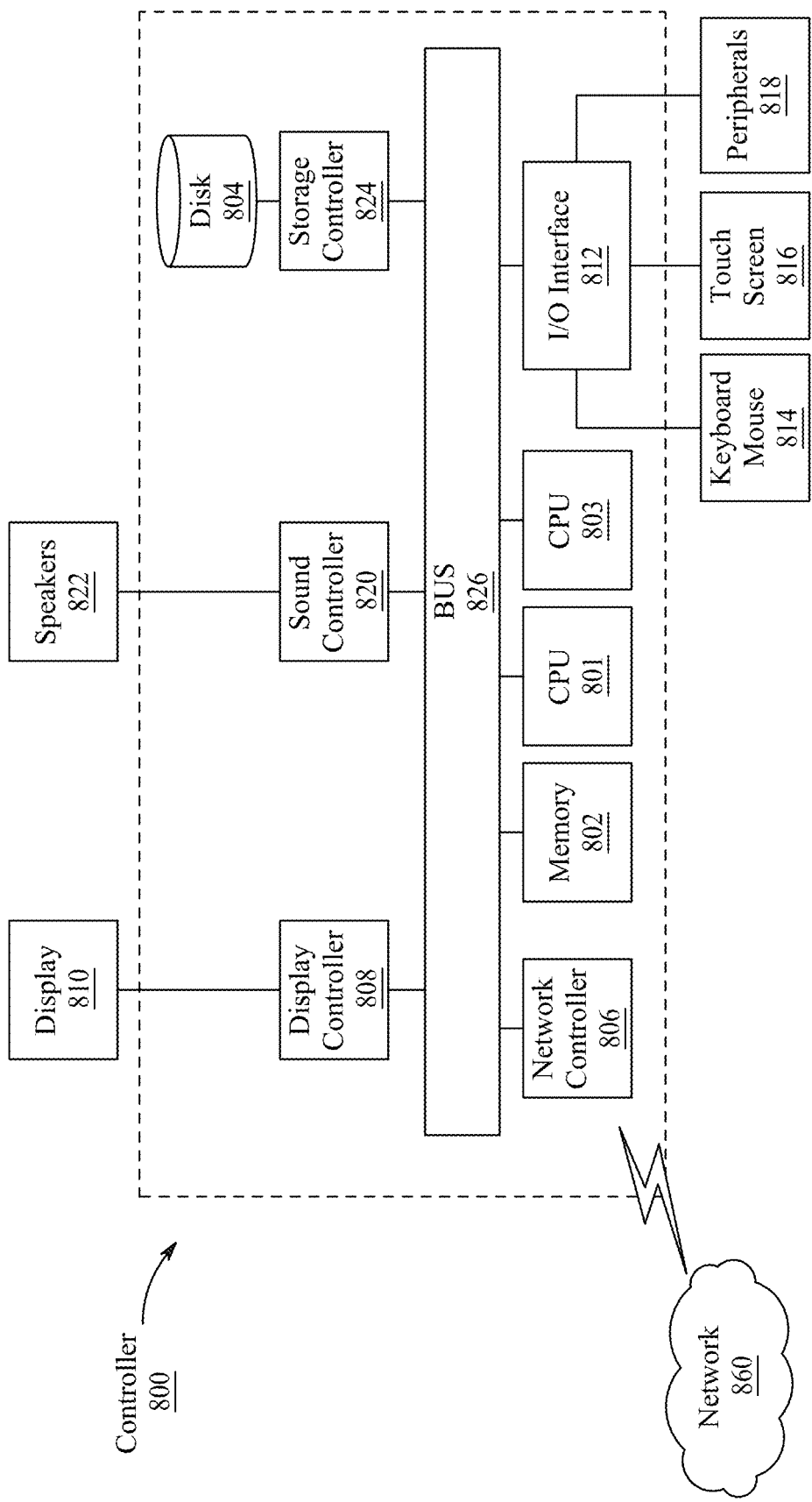
FIG. 8 is an illustration of a non-limiting example of details of computing hardware used in the computing system, according to certain embodiments.

In FIG. 8, a controller 800 is described as representative of the controller 750 of the system 700 for measuring glucose concentration of an analyte of FIG. 7. The controller 800 is a computing device which includes a CPU 801 which performs the processes described above/below. FIG. 8 is an illustration of a non-limiting example of details of computing hardware used in the computing system, according to exemplary aspects of the present disclosure. In FIG. 8, a controller 800 is described which is a computing device (that includes the controller 750) and includes a CPU 801 which performs the processes described above/below. The process data and instructions may be stored in memory 802. These processes and instructions may also be stored on a storage medium disk 804 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 801, 803 and an operating system such as Microsoft Windows 7, UNIX, Solaris, LINUX, Apple MAC-OS and other systems known to those skilled in the art.

The hardware elements in order to achieve the computing device may be realized by various circuitry elements, known to those skilled in the art. For example, CPU 801 or CPU 803 may be a Xenon or Core processor from Intel of America or an Opteron processor from AMD of America, or may be other processor types that would be recognized by one of ordinary skill in the art. Alternatively, the CPU 801, 803 may be implemented on an FPGA, ASIC, PLD or using discrete logic circuits, as one of the ordinary skill in the art would recognize. Further, CPU 801, 803 may be implemented as multiple processors cooperatively working in parallel to perform the instructions of the inventive processes described above.

The computing device in FIG. 8 also includes a network controller 806, such as an Intel Ethernet PRO network interface card from Intel Corporation of America, for interfacing with network 860. As can be appreciated, the network 860 can be a public network, such as the Internet, or a private network such as an LAN or WAN network, or any combination thereof and can also include PSTN or ISDN sub-networks. The network 860 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 808, such as a NVIDIA GeForce GTX or Quadro graphics adaptor from NVIDIA Corporation of America for interfacing with display 810, such as a Hewlett Packard HPL2445w LCD monitor. A general purpose I/O interface 812 interfaces with a keyboard and/or mouse 814 as well as a touch screen panel 816 on or separate from display 810. General purpose I/O interface also connects to a variety of peripherals 818 including printers and scanners, such as an OfficeJet or DeskJet from Hewlett Packard.

A sound controller 820 is also provided in the computing device such as Sound Blaster X-Fi Titanium from Creative, to interface with speakers/microphone 822 thereby providing sounds and/or music.

The general-purpose storage controller 824 connects the storage medium disk 804 with communication bus 826, which may be an ISA, EISA, VESA, PCI, or similar, for interconnecting all of the components of the computing device. A description of the general features and functionality of the display 810, keyboard and/or mouse 814, as well as the display controller 808, storage controller 824, network controller 806, sound controller 820, and general purpose I/O interface 812 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 9.

Figure 9:
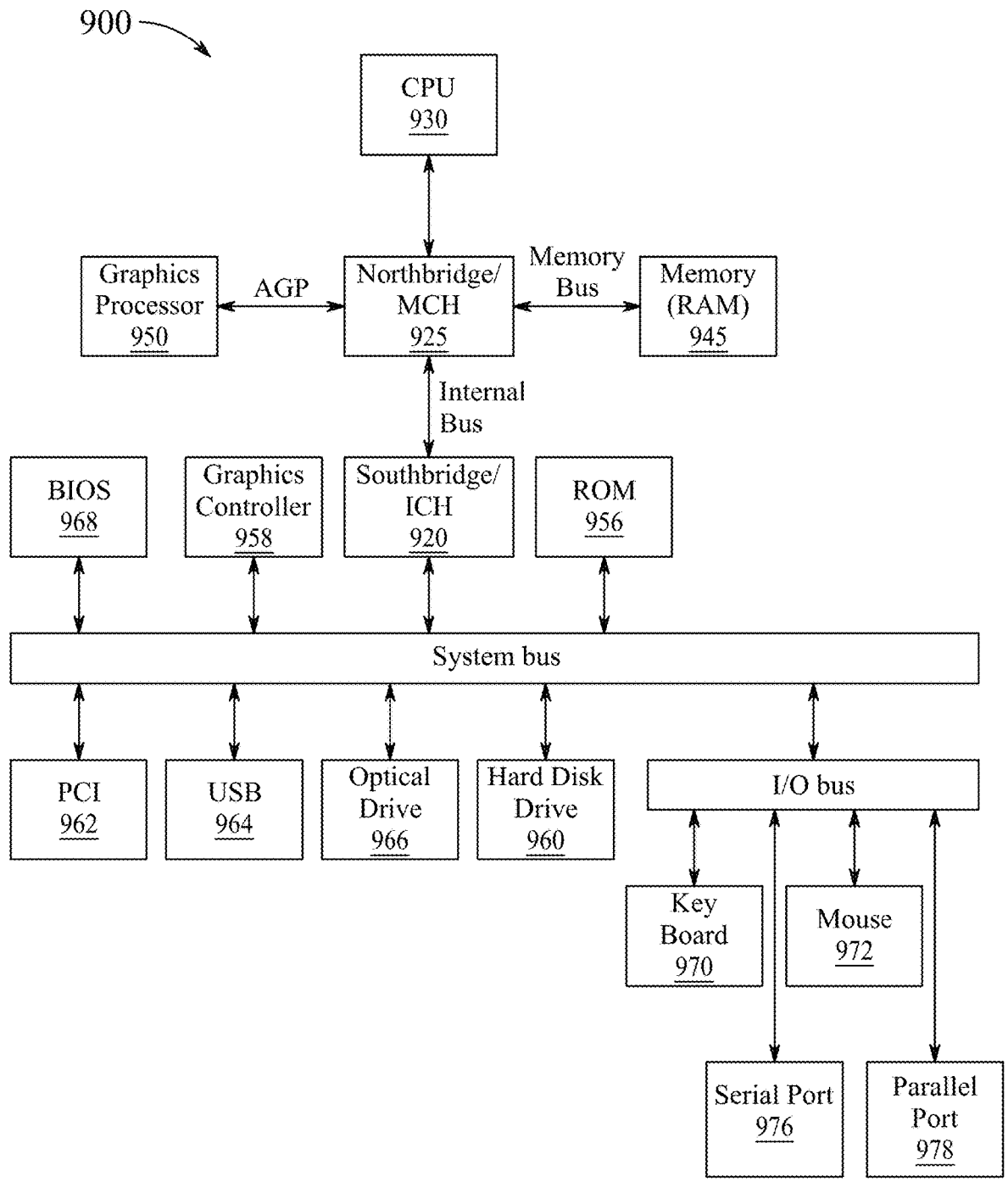
FIG. 9 is an exemplary schematic diagram of a data processing system used within the computing system, according to certain embodiments.

FIG. 9 shows a schematic diagram of a data processing system 900 used within the computing system, according to exemplary aspects of the present disclosure. The data processing system 900 is an example of a computer in which code or instructions implementing the processes of the illustrative aspects of the present disclosure may be located.

In FIG. 9, data processing system 980 employs a hub architecture including a north bridge and memory controller hub (NB/MCH) 925 and a south bridge and input/output (I/O) controller hub (SB/ICH) 920. The central processing unit (CPU) 930 is connected to NB/MCH 925. The NB/MCH 925 also connects to the memory 945 via a memory bus, and connects to the graphics processor 950 via an accelerated graphics port (AGP). The NB/MCH 925 also connects to the SB/ICH 920 via an internal bus (e.g., a unified media interface or a direct media interface). The CPU Processing unit 930 may contain one or more processors and even may be implemented using one or more heterogeneous processor systems.

Figure 10:
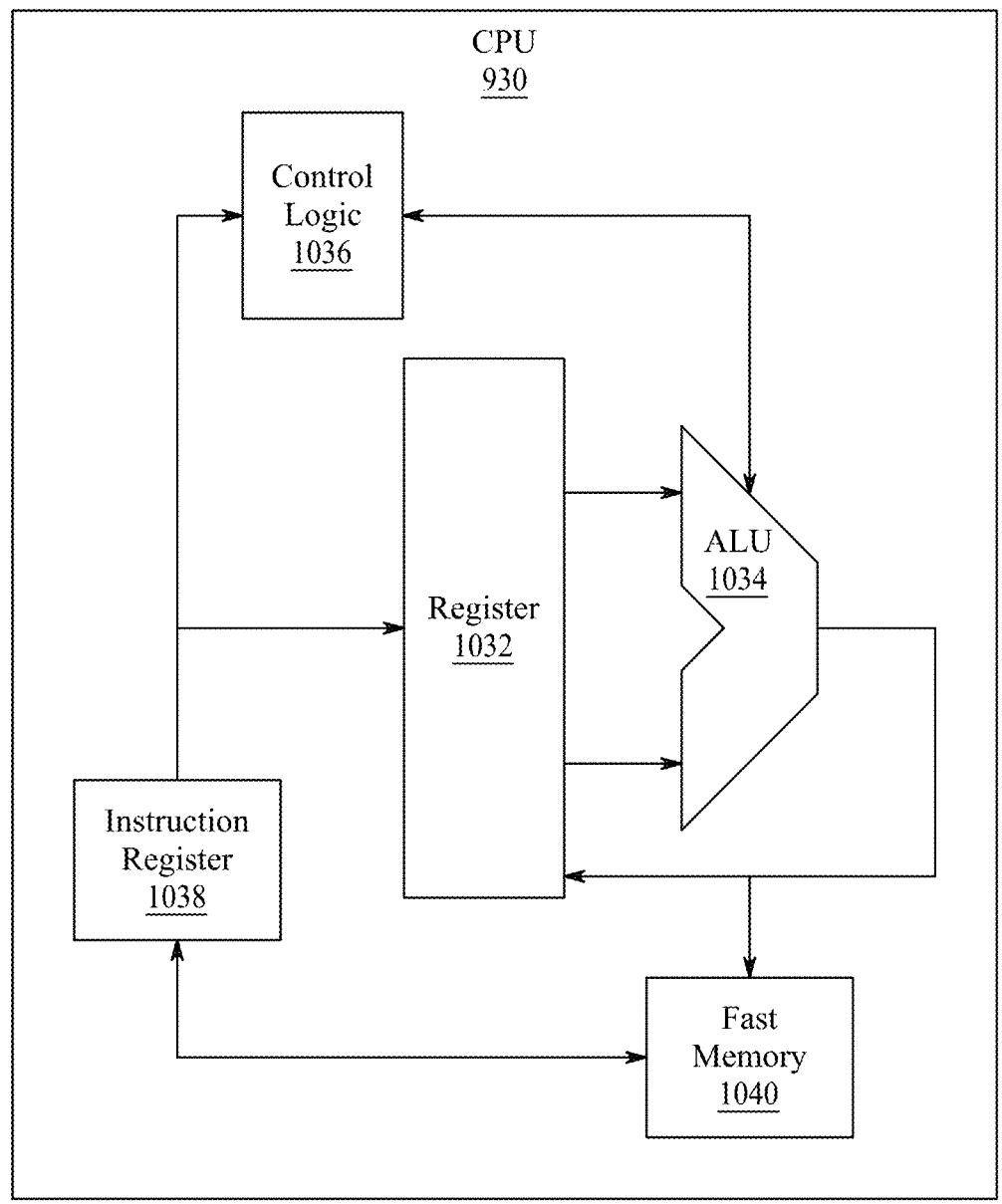
FIG. 10 is an exemplary schematic diagram of a processor used with the computing system, according to certain embodiments.

For example, FIG. 10 shows one aspects of the present disclosure of CPU 930. In one aspects of the present disclosure, the instruction register 1038 retrieves instructions from the fast memory 1040. At least part of these instructions is fetched from the instruction register 1038 by the control logic 1036 and interpreted according to the instruction set architecture of the CPU 930. Part of the instructions can also be directed to the register 1032. In one aspects of the present disclosure the instructions are decoded according to a hardwired method, and in another aspect of the present disclosure the instructions are decoded according to a microprogram that translates instructions into sets of CPU configuration signals that are applied sequentially over multiple clock pulses. After fetching and decoding the instructions, the instructions are executed using the arithmetic logic unit (ALU) 1034 that loads values from the register 1032 and performs logical and mathematical operations on the loaded values according to the instructions. The results from these operations can be feedback into the register and/or stored in the fast memory 1040. According to certain aspects of the present disclosures, the instruction set architecture of the CPU 930 can use a reduced instruction set architecture, a complex instruction set architecture, a vector processor architecture, a very large instruction word architecture. Furthermore, the CPU 930 can be based on the Von Neuman model or the Harvard model. The CPU 930 can be a digital signal processor, an FPGA, an ASIC, a PLA, a PLD, or a CPLD. Further, the CPU 930 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 9, the data processing system 980 can include that the SB/ICH 920 is coupled through a system bus to an I/O Bus, a read only memory (ROM) 956, universal serial bus (USB) port 964, a flash binary input/output system (BIOS) 968, and a graphics controller 958. PCI/PCIe devices can also be coupled to SB/ICH 920 through a PCI bus 962.

The PCI devices may include, for example, Ethernet adapters, add-in cards, and PC cards for notebook computers. The Hard disk drive 960 and CD-ROM 956 can use, for example, an integrated drive electronics (IDE) or serial advanced technology attachment (SATA) interface. In one aspect of the present disclosure the I/O bus can include a super I/O (SIO) device.

Further, the hard disk drive (HDD) 960 and optical drive 966 can also be coupled to the SB/ICH 920 through a system bus. In one aspects of the present disclosure, a keyboard 970, a mouse 972, a parallel port 978, and a serial port 976 can be connected to the system bus through the I/O bus. Other peripherals and devices that can be connected to the SB/ICH 920 using a mass storage controller such as SATA or PATA, an Ethernet port, an ISA bus, an LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Figure 11:
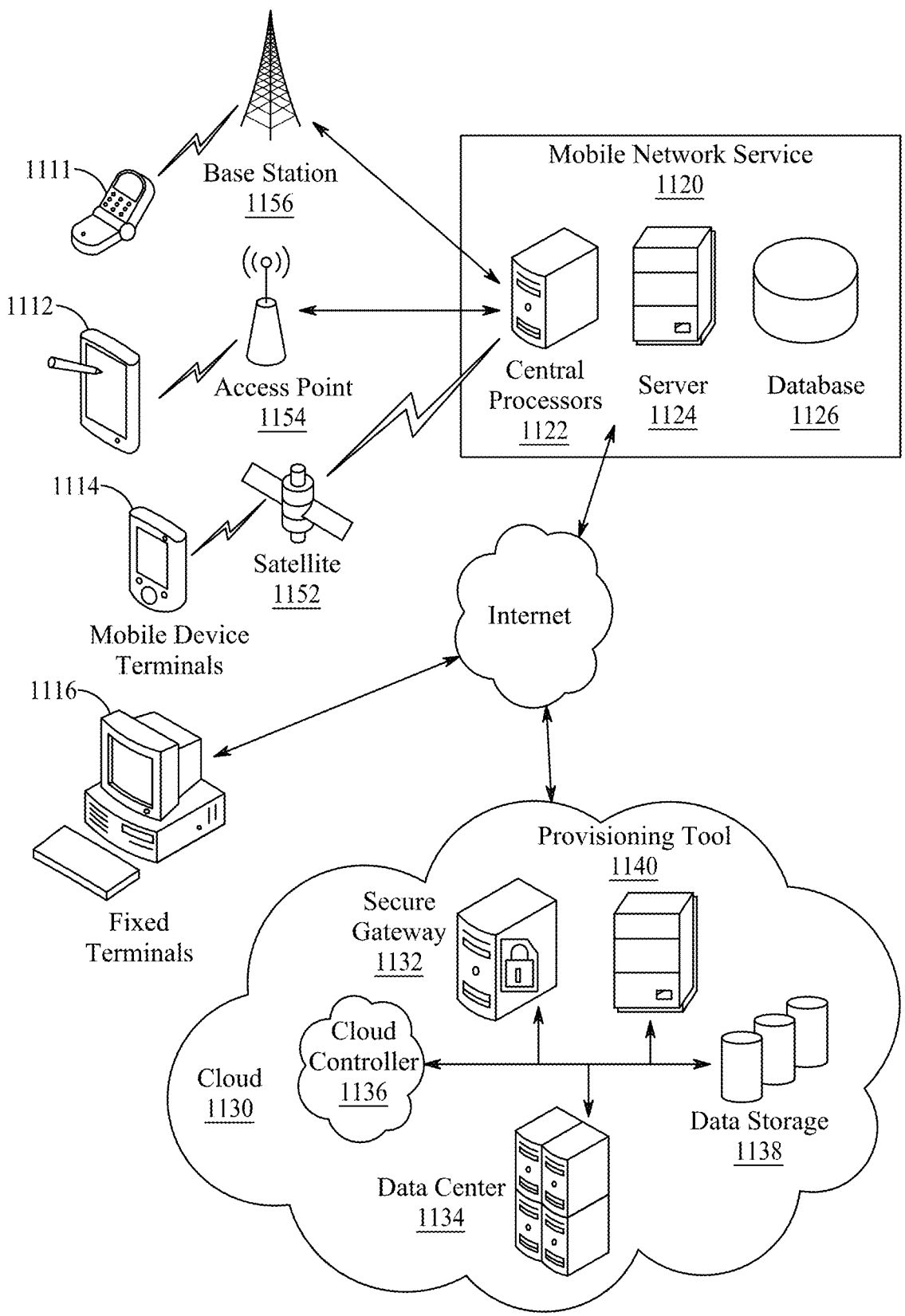
FIG. 11 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 11, in addition to various human interface and communication devices (e.g., display monitors, smart phones, tablets, personal digital assistants (PDAs)). More specifically, FIG. 11 illustrates client devices including smart phone 1111, tablet 1112, mobile device terminal 1114 and fixed terminals 1116. These client devices may be commutatively coupled with a mobile network service 1120 via base station 1156, access point 1154, satellite 1152 or via an internet connection. Mobile network service 1120 may comprise central processors 1122, server 1124 and database 1126. Fixed terminals 1116 and mobile network service 1120 may be commutatively coupled via an internet connection to functions in cloud 1130 that may comprise security gateway 1132, data center 1134, cloud controller 1136, data storage 1138 and provisioning tool 1140. The network may be a private network, such as a LAN or WAN, or may be a public network, such as the Internet. Input to the system may be received via direct user input and received remotely either in real-time or as a batch process. Additionally, some aspects of the present disclosures may be performed on modules or hardware not identical to those described. Accordingly, other aspects of the present disclosures are within the scope that may be claimed.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. An asymmetric S-shaped complementary metasurface biosensor for sensing glucose concentration, comprising:
    a metallic sheet configured to receive a glucose sample;
    a first arm configured as an S-shaped slot in the metallic sheet, wherein the first arm is configured to have a length $l_1$ and a width equal to one half of the length $l_1$;
    a second arm spaced apart from the first arm by a gap g, wherein the second arm is configured to be an S-shaped slot in the metallic sheet which is a mirror image of the first arm, wherein the second arm is configured to have a length $l_2$, wherein the length $l_2=l_1-d$, where d ranges from about 1% of $l_1$ to about 15% of $l_1$, and to have a width equal to one half of the length $l_2$; and
    wherein the first arm and the second arm are configured to resonate at an asymmetric resonant frequency when a terahertz radiation is swept in a direction normal to the metallic sheet,
    wherein a redshift in the asymmetric resonant frequency is indicative of a glucose concentration in the glucose sample.

2. The asymmetric S-shaped complementary metasurface biosensor of claim 1, wherein:
    a width of the slots of the first and second arms is about 3 microns;
    the length $l_1$ is about 140 microns;
    the length $l_2$ is selected from a range of about 120 microns to about 139 microns;
    the gap is about 4.5 microns; and
    the metallic sheet has a thickness of about 200 nanometers and is configured in a square shape having a length p of about 200 microns.

3. The asymmetric S-shaped complementary metasurface biosensor of claim 1, wherein the metallic sheet is configured to receive the glucose sample at a front surface of the metallic sheet.

4. The asymmetric S-shaped complementary metasurface biosensor of claim 1, wherein the metallic sheet is configured to be immersed in the glucose sample such that a front surface and a back surface of the metallic sheet contact the glucose sample.

5. The asymmetric S-shaped complementary metasurface biosensor of claim 1, further comprising:
a transparent casing configured to hold the metallic sheet; and
an opening located in the transparent casing to receive the glucose sample, wherein the transparent casing is configured such that the glucose sample coats at least one of the front surface and the back surface of the metallic sheet.

6. The asymmetric S-shaped complementary metasurface biosensor of claim 1, further comprising:
a casing configured to hold the metallic sheet; and
an opening located in the casing, wherein the opening is configured to receive the glucose sample, wherein the casing is configured such that the glucose sample coats both the front surface and the back surface of the metallic sheet.

7. The asymmetric S-shaped complementary metasurface biosensor of claim 1, the metallic sheet comprising:
a first edge, a second edge parallel to the first edge, a third edge perpendicular to the first edge and the second edge, a fourth edge parallel to the third edge, a first central axis extending from the first edge to the second edge, and a second central axis extending from the third edge to the fourth edge.

8. The asymmetric S-shaped complementary metasurface biosensor of claim 7, wherein the first arm further comprises:
a first leg coincident with the second central axis, wherein a first end of the first leg is configured to begin at a distance of ½ g from the first central axis and extend towards the third edge for a distance of $l_1/2$;
a second leg having a first end connected to a second end of the first leg, wherein the second leg is perpendicular to the first leg, wherein the second leg is configured to extend towards the first edge for a distance of $l_1/2$;
a third leg parallel to the first leg, wherein the third leg has a first end connected to a second end of the second leg, wherein the third leg is perpendicular to the second leg, wherein the third leg is configured to extend towards the first central axis for a distance of $l_1/2$;
a fourth leg having a first end connected to the first end of the first leg, wherein the fourth leg is perpendicular to the first leg, wherein the fourth leg is configured to extend towards the second edge for a distance of $l_1/2$; and
a fifth leg parallel to the first leg, wherein the fifth leg has a first end connected to a second end of the fourth leg, wherein the fifth leg is perpendicular to the fourth leg, wherein the fifth leg is configured to extend towards the third edge for a distance of $l_1/2$.

9. The asymmetric S-shaped complementary metasurface biosensor of claim 7, wherein the second arm further comprises:
a first leg coincident with the second central axis, wherein a first end of the first leg is configured to begin at a distance of ½ g from the first central axis and extend towards the fourth edge for a distance of $l_2/2$;
a second leg having a first end connected to a second end of the first leg, wherein the second leg is perpendicular to the first leg, wherein the second leg is configured to extend towards the first edge for a distance of $l_2/2$;
a third leg parallel to the first leg, wherein the third leg has a first end connected to a second end of the second leg, wherein the third leg is perpendicular to the second leg, wherein the third leg is configured to extend towards the first central axis for a distance of $l_2/2$;
a fourth leg having a first end connected to the first end of the first leg, wherein the fourth leg is perpendicular to the first leg, wherein the fourth leg is configured to extend towards the second edge for a distance of $l_2/2$; and
a fifth leg parallel to the first leg, wherein the fifth leg has a first end connected to a second end of the fourth leg, wherein the fifth leg is perpendicular to the fourth leg, wherein the fifth leg is configured to extend towards the fourth edge for a distance of $l_2/2$.

10. The asymmetric S-shaped complementary metasurface biosensor of claim 1, wherein the metallic sheet is an aluminum sheet.

11. The asymmetric S-shaped complementary metasurface biosensor of claim 1, wherein the metallic sheet is one of an aluminum sheet, a gold sheet, a graphene sheet and a silver sheet.

12. A system for measuring glucose concentration of an analyte, comprising:
an asymmetric S-shaped complementary metasurface biosensor including:
a metallic sheet configured to receive a glucose sample;
a first arm configured as an S-shaped slot in the metallic sheet, wherein the first arm has a length $l_1$ and a width equal to one half of the length $l_1$;
a second arm spaced apart from the first arm by a gap g, wherein the second arm is configured to be an S-shaped slot in the metallic sheet which is a mirror image of the first arm, wherein the second arm has a length $l_2$, wherein the length $l_2=l_1-d$, where d ranges from about 1% of $l_1$ to about 15% of $l_1$, and to have a width equal to one half of the length $l_2$;
a terahertz radiation source configured to sweep a terahertz radiation beam at the range of frequencies in a normal direction to the metallic sheet such that an electromagnetic coupling between the first arm and the second arm excites an asymmetric resonance frequency;
a terahertz receiver configured to receive light beams transmitted through the asymmetric S-shaped complementary metasurface biosensor and generate electrical signals indicative of a redshift in the asymmetric resonance frequency response;
a database including records relating the redshift to glucose concentration in the analyte;
a controller operatively connected to the terahertz radiation source, the terahertz radiation receiver, and the database, wherein the controller includes circuitry, a memory storing program instructions and at least one processor configured to execute the program instructions to:
activate the terahertz radiation source to project the terahertz radiation beam at the range of frequencies onto the metallic sheet;
receive the electrical signals from the receiver; and
match the redshift to a record in the database which identifies the glucose concentration of the analyte.

13. The system of claim 12, further comprising:
a transparent casing configured to hold the metallic sheet; and
an opening located in the transparent casing to receive the glucose sample,
wherein the transparent casing is configured such that the glucose sample coats at least one of the front surface and the back surface of the metallic sheet.

14. The system of claim 12, wherein the metallic sheet comprises:
a first edge, a second edge parallel to the first edge, a third edge perpendicular to the first edge and the second edge, a fourth edge parallel to the third edge, a first central axis extending from the first edge to the second edge, and a second central axis extending from the third edge to the fourth edge.

15. The system of claim 14, wherein the first arm further comprises:
a first leg coincident with the second central axis, wherein a first end of the first leg is configured to begin at a distance of ½ g from the first central axis and extend towards the third edge for a distance of $l_1/2$;
a second leg having a first end connected to a second end of the first leg, wherein the second leg is perpendicular to the first leg, wherein the second leg is configured to extend towards the first edge for a distance of $l_1/2$;
a third leg parallel to the first leg, wherein the third leg has a first end connected to a second end of the second leg, wherein the third leg is perpendicular to the second leg, wherein the third leg is configured to extend towards the first central axis for a distance of $l_1/2$;
a fourth leg having a first end connected to the first end of the first leg, wherein the fourth leg is perpendicular to the first leg, wherein the fourth leg is configured to extend towards the second edge for a distance of $l_1/2$; and
a fifth leg parallel to the first leg, wherein the fifth leg has a first end connected to a second end of the fourth leg, wherein the fifth leg is perpendicular to the fourth leg, wherein the fifth leg is configured to extend towards the third edge for a distance of $l_1/2$.

16. The system of claim 14, wherein the second arm further comprises:
a first leg coincident with the second central axis, wherein a first end of the first leg is configured to begin at a distance of ½ g from the first central axis and extend towards the fourth edge for a distance of $l_2/2$;
a second leg having a first end connected to a second end of the first leg, wherein the second leg is perpendicular to the first leg, wherein the second leg is configured to extend towards the first edge for a distance of $l_2/2$;
a third leg parallel to the first leg, wherein the third leg has a first end connected to a second end of the second leg, wherein the third leg is perpendicular to the second leg, wherein the third leg is configured to extend towards the first central axis for a distance of $l_2/2$;
a fourth leg having a first end connected to the first end of the first leg, wherein the fourth leg is perpendicular to the first leg, wherein the fourth leg is configured to extend towards the second edge for a distance of $l_2/2$; and
a fifth leg parallel to the first leg, wherein the fifth leg has a first end connected to a second end of the fourth leg, wherein the fifth leg is perpendicular to the fourth leg, wherein the fifth leg is configured to extend towards the fourth edge for a distance of $l_2/2$.

17. The system of claim 12, wherein the metallic sheet is one of an aluminum sheet, a gold sheet, a graphene sheet and a silver sheet.

18. A sensor system for determining a concentration of an analyte in a test sample, comprising:
an asymmetric S-shaped complementary metasurface sensor including:
a metallic sheet comprising a first edge, a second edge parallel to the first edge, a third edge perpendicular to the first edge and the second edge, a fourth edge parallel to the third edge, a first central axis extending from the first edge to the second edge, and a second central axis extending from the third edge to the fourth edge;
a transparent casing configured to hold the metallic sheet;
an opening located in the transparent casing to receive the test sample,
wherein the transparent casing is configured such that the glucose sample coats at least one of the front surface and the back surface of the metallic sheet;
a first arm configured as an S-shaped slot in the metallic sheet, wherein the first arm has a length $l_1$ and a width equal to one half of the length $l_1$;
a second arm spaced apart from the first arm by a gap g, wherein the second arm is configured as an S-shaped slot in the metallic sheet which is a mirror image of the first arm, wherein the second arm has a length $l_2$, wherein the length $l_2=l_1-d$, where d ranges from about 1% of $l_1$ to about 15% of $l_1$, and to have a width equal to one half of the length $l_2$;
a terahertz radiation source having a range of frequencies, wherein the terahertz radiation source is configured to sweep a terahertz radiation beam at the range of frequencies normal to the metallic sheet such that such that an electromagnetic coupling between the first arm and the second arm excites an asymmetric resonance frequency;
a terahertz receiver configured to receive light beams transmitted through the asymmetric S-shaped complementary metasurface biosensor and generate electrical signals indicative of a redshift in the asymmetric resonance frequency;
a database including records relating the redshift to the concentration of the analyte in the test sample;
a controller operatively connected to the terahertz radiation source, the terahertz radiation receiver, and the database, wherein the controller has circuitry, a memory storing program instructions and at least one processor configured to execute the program instructions to:
activate the terahertz radiation source to project the terahertz radiation beam at the range of frequencies onto the metallic sheet;
receive the electrical signals from the receiver; and
match the redshift to a record in the database which identifies the analyte concentration.

19. The system of claim 18, wherein the first arm further comprises:
a first leg coincident with the second central axis, wherein a first end of the first leg is configured to begin at a distance of ½ g from the first central axis and extend towards the third edge for a distance of $l_1/2$;
a second leg having a first end connected to a second end of the first leg, wherein the second leg is perpendicular to the first leg, wherein the second leg is configured to extend towards the first edge for a distance of $l_1/2$;

a third leg parallel to the first leg, wherein the third leg has a first end connected to a second end of the second leg, wherein the third leg is perpendicular to the second leg, wherein the third leg is configured to extend towards the first central axis for a distance of $l_1/2$;

a fourth leg having a first end connected to the first end of the first leg, wherein the fourth leg is perpendicular to the first leg, wherein the fourth leg is configured to extend towards the second edge for a distance of $l_1/2$; and a fifth leg parallel to the first leg, wherein the fifth leg has a first end connected to a second end of the fourth leg, wherein the fifth leg is perpendicular to the fourth leg, wherein the fifth leg is configured to extend towards the third edge for a distance of $l_1/2$.

20. The system of claim 18, wherein the second arm further comprises:

a first leg coincident with the second central axis, wherein a first end of the first leg is configured to begin at a distance of ½ g from the first central axis and extend towards the fourth edge for a distance of $l_2/2$;

a second leg having a first end connected to a second end of the first leg, wherein the second leg is perpendicular to the first leg, wherein the second leg is configured to extend towards the first edge for a distance of $l_2/2$;

a third leg parallel to the first leg, wherein the third leg has a first end connected to a second end of the second leg, wherein the third leg is perpendicular to the second leg, wherein the third leg is configured to extend towards the first central axis for a distance of $l_2/2$;

a fourth leg having a first end connected to the first end of the first leg, wherein the fourth leg is perpendicular to the first leg, wherein the fourth leg is configured to extend towards the second edge for a distance of $l_2/2$; and a fifth leg parallel to the first leg, wherein the fifth leg has a first end connected to a second end of the fourth leg, wherein the fifth leg is perpendicular to the fourth leg, wherein the fifth leg is configured to extend towards the fourth edge for a distance of $l_2/2$.

\* \* \* \* \*